(12) United States Patent
Utsi et al.

(10) Patent No.: US 8,718,787 B2
(45) Date of Patent: May 6, 2014

(54) WIRELESS COMMUNICATION WITH A MEDICAL IMPLANT

(75) Inventors: Vincent Utsi, Ely (GB); Mark Norris, Cambridge (GB); Jean-Daniel Richerd, Cambridge (GB)

(73) Assignee: MicroCHIPS, Inc., Lexington, MA (US)

( * ) Notice: Subject to any disclaimer, the term of this patent is extended or adjusted under 35 U.S.C. 154(b) by 0 days.

(21) Appl. No.: 13/610,394

(22) Filed: Sep. 11, 2012

(65) Prior Publication Data

US 2013/0002496 A1 Jan. 3, 2013

Related U.S. Application Data

(62) Division of application No. 12/334,196, filed on Dec. 12, 2008, now Pat. No. 8,285,387.

(51) Int. Cl.
*A61N 1/02* (2006.01)
*A61N 1/372* (2006.01)

(52) U.S. Cl.
CPC .................................. *A61N 1/37223* (2013.01)
USPC .......................................................... 607/60

(58) Field of Classification Search
None
See application file for complete search history.

(56) References Cited

U.S. PATENT DOCUMENTS

| | | | |
|---|---|---|---|
| 2,258,974 A | 10/1941 | Dagnall | |
| 2,445,895 A | 7/1948 | Tyrrell | |
| 3,034,076 A | 5/1962 | Tomiyasu | |
| 3,656,162 A | 4/1972 | Mee | |
| 3,838,362 A | 9/1974 | Kurtz | |
| 4,356,492 A | 10/1982 | Kaloi | |
| 5,861,019 A | 1/1999 | Sun et al. | |
| 6,115,636 A * | 9/2000 | Ryan | 607/60 |
| 6,307,525 B1 | 10/2001 | Bateman et al. | |
| 6,567,053 B1 | 5/2003 | Yablonovitch et al. | |

(Continued)

FOREIGN PATENT DOCUMENTS

| | | |
|---|---|---|
| EP | 0978895 A2 | 2/2000 |
| EP | 0871238 A2 | 5/2003 |
| JP | 60 134605 A | 7/1985 |
| WO | 01/63699 A3 | 8/2001 |

OTHER PUBLICATIONS

International Search Report and Written Opinion for International Application No. PCT/US2009/067637 mailed Aug. 12, 2010.

(Continued)

*Primary Examiner* — Kennedy Schaetzle
(74) *Attorney, Agent, or Firm* — Sutherland Asbill & Brennan LLP

(57) ABSTRACT

An apparatus for providing transdermal wireless communication includes medical implant circuitry; a transceiver coupled to the medical implant circuitry; a first metal surface having an end portion and a base portion; a second metal surface parallel to the first metal surface and connected to the first metal surface by a conductor, the second metal surface being separated from the first metal surface by a dielectric layer; a first radiating element tuned to a first frequency and disposed within the dielectric layer between the first metal surface and second metal surface; and a feed structure in electrical communication with the transceiver and the first radiating strip. The first radiating element has a first reactive portion at a first end thereof, a second reactive portion at a second end thereof, and a first radiating strip extending between the first reactive portion and the second reactive portion.

4 Claims, 23 Drawing Sheets

(56) References Cited

U.S. PATENT DOCUMENTS

| | | |
|---|---|---|
| 6,574,510 B2 | 6/2003 | VonArx et al. |
| 6,597,258 B2 | 7/2003 | Rosenbaum |
| 6,614,406 B2 | 9/2003 | Amundson et al. |
| 6,809,701 B2 | 10/2004 | Amundson et al. |
| 6,885,355 B2 * | 4/2005 | Killen et al. ............ 343/909 |
| 7,148,803 B2 | 12/2006 | Bandy et al. |
| 7,149,578 B2 | 12/2006 | Edvardsson |
| 2003/0216793 A1 | 11/2003 | Karlsson et al. |

OTHER PUBLICATIONS

LaBranche et al., 1997, "Next-Generation, Advanced thick Film Multilayer System," IEMT/IMC Proceedings, pp. 72-77.

Non-Final Office Action dated May 11, 2010 for U.S. Appl. No. 12/334,184 (12 pages).

\* cited by examiner

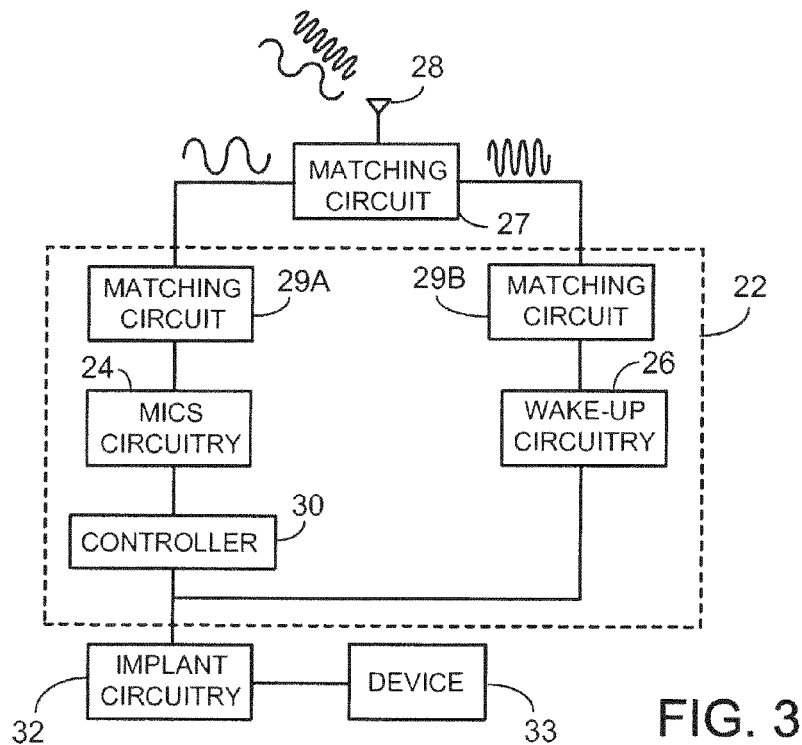
FIG. 3
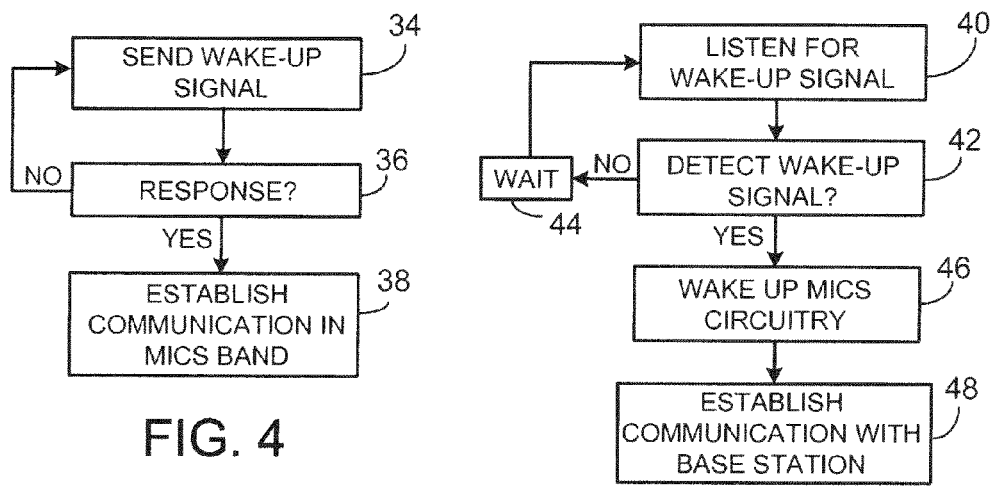
FIG. 4
FIG. 5

WIRELESS COMMUNICATION WITH A MEDICAL IMPLANT

CROSS-REFERENCE TO RELATED APPLICATIONS

This application is a divisional of U.S. application Ser. No. 12/334,196, filed Dec. 12, 2008, now issued as U.S. Pat. No. 8,285,387, which is incorporated herein by reference in its entirety.

TECHNICAL FIELD

This invention relates to medical implants, and more particularly to communication with a medical implant.

BACKGROUND

Among the known medical implants are those that either receive information from a transmitter outside the body or transmit information to a receiver located outside the body. Such communication is most conveniently carried out by causing electromagnetic waves to propagate between an intra-corporal medical implant and an extra-corporal base station.

A difficulty with the use of electromagnetic waves arises from their tendency to be attenuated when traveling within the human body. Although attenuation decreases with increasing wavelengths, the use of longer wavelengths typically requires the use of large antennas.

In 1999, the United States Federal Communication Commission ("FCC") allocated the Medical Implant Communication Service ("MICS") band, which extends between 402 MHz and 405 MHz, as available for use by medical implants. Although the MICS band represents an attempt at compromise, it is still the case that body tissues significantly attenuate electromagnetic waves propagating at MICS frequencies. As a result, the distance between the base station and the implant must be small. In fact, in many applications, the base station's receiving antenna is placed on or within inches of the skin.

The limited range of known medical implant communication systems poses few problems when one wishes to establish communication with an implant infrequently. For example, if one only needed to communicate with an implant during a monthly clinical appointment, it would not be inconvenient to have to hold a receiver next to the skin for short periods.

However, in some applications, one would like to communicate periodically or intermittently with an implant over an extended period. For example, one might need to monitor a measured value at frequent times or may need to cause an implant to release a drug at certain times or in response to certain conditions.

Under the foregoing conditions, it would be convenient to establish communication between an implant and a base station within the same room as a patient, but in some unknown and changing direction and distance relative to the patient.

In principle, one could extend the communication range of an implant by transmitting with more power. One difficulty that arises, however, is that the FCC imposes a limit on the amount of power that can be transmitted. Another difficulty that arises is that the implant's power supply is finite, and high power transmission is apt to drain it more quickly.

An exemplary telemetry apparatus for an implantable medical device is that described in U.S. Pat. No. 6,574,203 (Von Arx).

Antennas for implantable medical devices are disclosed in U.S. Pat. No. 6,809,701 (Amundson et al.), U.S. Pat. No. 7,149,578 (Edvardsson), U.S. Pat. No. 5,861,019 (Sun et al.), and U.S. Patent Publication 2005/0154428 (Bruinsma).

SUMMARY

The invention is based on the recognition that a non-omnidirectional antenna on a medical implant will interact with the patient's body in such a way as to yield a nearly omnidirectional radiation pattern.

In one aspect, the invention features an apparatus for providing transdermal wireless communication. The apparatus includes medical implant circuitry, a transceiver coupled to the medical implant circuitry, a first metal surface having an end portion and a base portion, a second metal surface parallel to the first metal surface and connected to the first metal surface by a conductor, and separated from the first metal surface by a dielectric layer, a first radiating element tuned to a first frequency and disposed within the dielectric layer between the first metal surface and second metal surface. The first radiating element has a first reactive portion at a first end thereof, a second reactive portion at a second end thereof, and a first radiating strip extending between the first reactive portion and the second reactive portion. The apparatus further includes a feed structure in electrical communication with the transceiver and the first radiating strip.

In some embodiments, the first reactive portion includes a first capacitive structure, and the second reactive portion includes a second capacitive structure.

In other embodiments, the first reactive portion includes a first conductive planar portion having a dimension in excess of a width of the first radiating strip, and the second reactive portion includes a second conductive planar portion having a dimension in excess of the width of the first radiating strip.

Alternative embodiments include those in which the first reactive portion includes an inductive structure, and those in which the first reactive portion includes a first conducting strip disposed to follow a first serpentine path, and the second reactive portion includes a second conducting strip disposed to follow a second serpentine path, as well as those in which the first reactive portion of the first radiating element includes an inductive structure and the second reactive portion includes a capacitive structure.

Yet other embodiments include those in which the feed structure is separated from the first radiating strip by a dielectric, and those in which the feed structure is capacitively coupled to the first radiating strip.

Other embodiments include a second radiating element tuned to a second frequency and disposed between the first reactive portion of the first radiating element and the second reactive portion of the first radiating element. In some such embodiments, the feed structure can provide a signal of the first frequency and a signal of the second frequency to both the first radiating element and the second radiating element. In other such embodiments, the feed structure is capacitively coupled to both the first radiating element and the second radiating element. In yet other such embodiments, the second radiating element is tuned to a frequency between approximately 2 GHz and 2.5 GHz.

Yet other embodiments include those in which a planar surface forms the second metal surface. In some such embodiments, the planar surface includes a surface of a housing.

Other embodiments include those in which the second metal surface includes a planar surface of a housing.

In another embodiment, the end portion of the first metal surface is disposed over the first reactive portion of the first radiating element and the base portion of the first metal surface is disposed over the second reactive portion of the first radiating element.

Other embodiments include those in which the first radiating element defines a region at which an electric field supported by the first radiating element has its maximum amplitude, and in which at least one of the end portion and base portion is disposed over the defined region, those in which at least one of the end portion and base portion is disposed over a region at which a gradient vector of electric field amplitude reverses direction, those in which at least one of the end portion and base portion is disposed to intercept electric field lines in a region at which an electric field supported by the first radiating element reaches its maximum amplitude, and those in which at least one of the end portion and base portion is disposed to block a selected portion of an electric field supported by the first radiating element, with examples of the selected portion of the electric field including a portion having an amplitude in excess of a threshold, and a portion having a gradient vector that reverses direction.

Additional embodiments include those in which the first radiating element is tuned to a first frequency within the MICS band, and those in which the first radiating element is tuned to a first frequency between 400 MHz and 405 MHz.

At least one embodiment of the apparatus further includes a neck extending between the end portion and the base portion.

Other embodiments of the apparatus include those in which at least one of the first metal surface and the second metal surface includes a planar surface, those in which the first and second metal surfaces include grounded surfaces, and those in which the first and second metal surfaces include ground planes.

In another aspect, the invention features an apparatus for providing transdermal wireless communication in a selected direction, the apparatus including medical implant circuitry; a transceiver coupled to the medical implant circuitry; and a first metal surface disposed in a plane perpendicular to the selected direction. The first metal surface has an end portion, and a base portion. The apparatus further includes a first planar radiating element tuned to a first frequency and disposed on a dielectric layer above the first metal surface, the first planar radiating element having a first reactive portion at a first end thereof, a second reactive portion at a second end thereof, and a first planar radiating strip extending between the first reactive portion and the second reactive portion; and a feed structure in electrical communication with the transceiver and the first planar radiating strip for providing the carrier signal to the first planar radiating strip.

In some embodiments, the apparatus further includes a neck extending between the end portion and the base portion.

In yet another aspect, the invention features an apparatus for providing wireless communication across the skin of a patient, the apparatus including: medical implant circuitry; a transceiver coupled to the medical implant circuitry; a feed configured to receive a signal from the transceiver; a planar radiating element coupled to the feed; and a field stop disposed to block radiation from selected portions of an electric field distribution supported by the planar radiating element.

Another aspect of the invention is a method for providing transdermal communication, the method including causing a current on an antenna implanted inside a patient, the antenna supporting an electromagnetic field having a near-field component and a far-field component; shielding the near-field component, thereby trapping energy contained in the near-field component and reducing the extent to which the energy in the near-field component interacts with the patient; and allowing the propagation of the far-field component through the skin of the patient.

Practices of the method include those in which shielding the near-field component includes placing a conductive plane between a reactive portion of the antenna and the skin, those in which shielding the near-field component includes placing a conductive plane over a first end of the antenna and a second end of the antenna, and those that further include selecting the antenna to be a radiating strip.

Another aspect of the invention is a method of providing wireless communication between a medical implant and a base station across the skin of a patient in the presence of a mismatch between the permittivity of the patient's skin layer and the permittivity of a medium surrounding the patient. Such a method includes communicating with a transceiver of a medical implant that has been implanted under the skin of a patient; causing an antenna on the medical implant to launch an electromagnetic wave carrying energy, the energy having a first portion traveling in a first direction and a second portion traveling in a direction other than the first direction, the first and second portions having different magnitudes, wherein a portion of the first portion enters a layer of the patient and causes an endoperipheral wave that propagates within the peripheral layer, and wherein as the endoperipheral wave propagates within the peripheral layer, a portion of the energy carried by the endoperipheral wave exits the endoperipheral layer and enters a surrounding medium, the ratio of the portion of the energy that exits the skin layer being dependent on the extent of the mismatch between the permittivity of the endoperipheral layer and the permittivity of the surrounding medium.

Yet another aspect of the invention features a method of providing wireless communication between a medical implant in a patient and a base station. Such a method includes causing an antenna on the medical implant to launch a wave having a first portion in a first direction and a second portion in a second direction, the first and second portions having differing magnitudes, wherein a portion of the first portion enters a biological waveguide defined by a constituent of the body of the patient, the biological waveguide having a first permittivity that differs from the permittivity of the medium surrounding the base station; whereby the wave launched into the biological waveguide becomes a guided wave having an energy, and wherein as the guided wave propagates in the biological waveguide, a portion of the energy escapes the biological waveguide and enters the medium surrounding the base station; and wherein the ratio of energy escaping the biological waveguide to the energy remaining in the biological waveguide depends on the ratio between the permittivity of the biological waveguide and the permittivity of the medium surrounding the base station.

In one practice, the biological waveguide includes a portion of the skin.

Another aspect of the invention features a method of determining a preferred patient orientation for establishing communication between a medical implant inside a patient and a base station outside the patient. Such a method includes, following the healing of an incision caused by implantation of a medical implant inside a patient, determining an angle between an implant axis of the implant and a patient axis of the patient; on the basis of the angle, determining an optimal orientation of the patient relative to the base station for establishing wireless communication between the medical implant and the base station; and providing, to the patient, information representative of the optimal orientation.

In another aspect, the invention features an apparatus for providing energy to first and second antennas. The apparatus includes a first section of a microstrip transmission line, the first section extending from a feedpoint along an axis; a first load for coupling to the first antenna, the first load being connected to a distal end of the first section; a second section of microstrip transmission line, the second section extending along the axis and having a proximal end connected to the first pair of microstrip transmission line stubs; and a second load connected to a distal end of the second section for coupling to the second antenna; wherein the lengths of the first and second sections are selected to cause an electromagnetic wave having a first frequency to encounter an impedance mismatch at the first load and an impedance match at the second load, and to cause an electromagnetic wave having a second frequency to encounter an impedance mismatch at the second load and an impedance match at the first load.

In another aspect, the invention features an apparatus for providing energy to first and second antennas. The apparatus includes a first section of a microstrip transmission line, the first section extending from a feedpoint along an axis; a first load for coupling to the first antenna, the first load being connected to a distal end of the first section; a second section of microstrip transmission line extending from the feedpoint and along a direction parallel to and offset from the axis; and a second load for coupling to the second antenna, the second section being connected to a distal end of the second section; wherein the lengths of the first and second sections are selected to cause an electromagnetic wave having a first frequency to encounter an impedance mismatch at the first load and an impedance match at the second load, and to cause an electromagnetic wave having a second frequency to encounter an impedance mismatch at the second load and an impedance match at the first load.

In one embodiment, the apparatus includes a third section of microstrip transmission line extending from the feedpoint and along a direction parallel to and offset from the axis and offset from the second section, and a third load for coupling to the second antenna, the third section being connected to a distal end of the third section; wherein the lengths of the first, second, and third sections are selected to cause an electromagnetic wave having a first frequency to encounter an impedance mismatch at the first load and an impedance match at the second and third loads, and to cause an electromagnetic wave having a second frequency to encounter an impedance match at the first load and an impedance mismatch at the second and third loads.

The details of one or more embodiments of the invention are set forth in the accompanying drawings and the description below. Other features, objects, and advantages of the invention will be apparent from the description, the claims, and the drawings, in which:

DESCRIPTION OF DRAWINGS

FIG. 3 is a block diagram of the wireless communication system of the medical implant of FIG. 2;

FIG. 4 is a flow chart of a communication protocol carried out by the base station of FIG. 1;

FIG. 5 is a flow chart of a communication protocol carried out by the wireless communication system of FIG. 3;

Like reference symbols in the various drawings indicate like elements.

DETAILED DESCRIPTION

Figure 1:
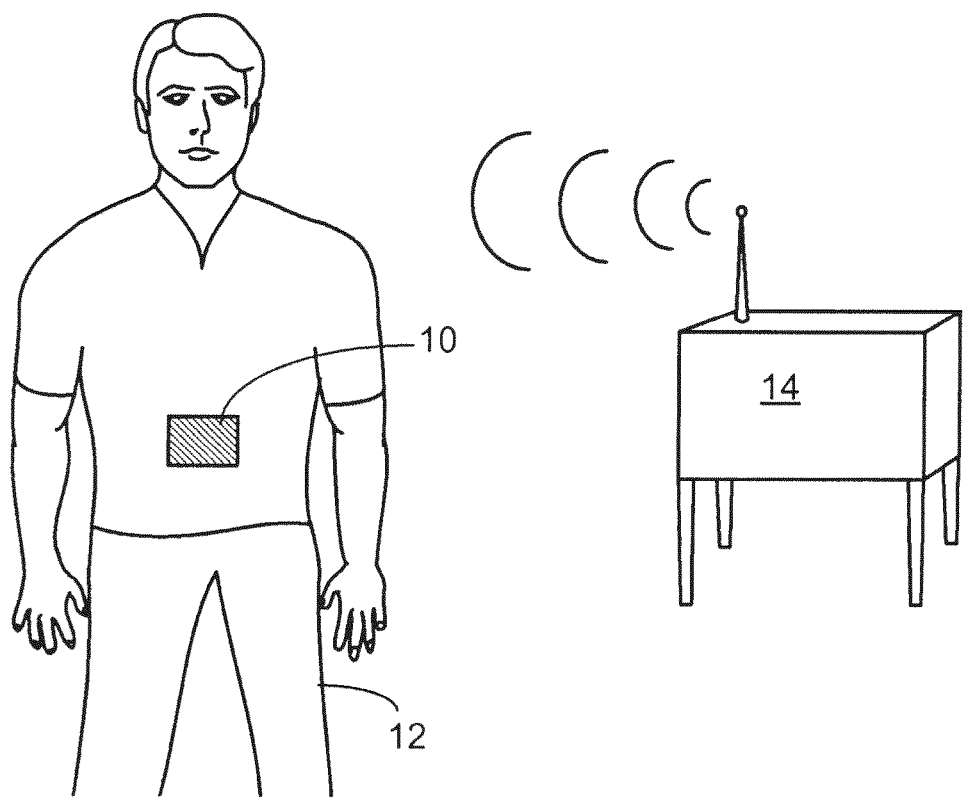
FIG. 1 shows a medical implant in communication with a base station.

FIG. 1 shows a medical implant 10, sometimes referred to as an "implantable medical device," in a patient 12. The medical implant 10 is one that either performs actions in response to instructions, transmits data, or both. For example, the medical implant 10 could be one that releases drugs in response to a stimulus. An example of an implant for controlled release or exposure of the contents of an implanted reservoir is described in U.S. Patent Pub. 2004/0121486 (Uhland et al.), entitled "Controlled Release Device and Method Using Electrothermal Ablation," the contents of which are herein incorporated by reference. The medical implant 10 could be one that performs physiological measurements, such as measuring glucose levels, cardiac signals, or blood pressure levels. One implant for measuring glucose is that disclosed in U.S. Patent Pub. 2005/0096587 (Santini), entitled "Medical Device for Sensing Glucose," the contents of which are incorporated herein by reference.

As used herein, the term "medical implant" refers to active implantable medical devices. An "active implantable medical device" is a medical device that uses electricity or other energy, and is partly or totally inserted into a human or animal body or a natural orifice by means of a surgical or medical procedure, and is typically expected to remain there for several days, weeks, months, or years after the procedure is completed. The term "medical device" refers to a manufactured product that is used to prevent, diagnose, treat, or monitor human or animal disease or injuries, or to investigate, replace, modify, or maintain anatomical structures or physiological functions. Manufactured products that achieve results by pharmacological, immunological, or metabolic means are not medical devices. However, the results achieved by medical devices may be assisted by these means. Representative examples of medical implants suitable for use in/with the present antenna devices and telemetry methods include pacemakers, cardioverter-defibrillators, nerve and muscle stimulators, deep brain stimulators, drug delivery devices (e.g., drug pumps), cardiomyostimulators, cochlear implants, artificial organs (e.g., artificial hearts), biological sensors, and cardiac and other physiologic monitors. The medical implant may provide of a combination of these functionalities. In one embodiment, the medical implant comprises a multi-reservoir containment device for the controlled in vivo exposure or release of reservoir contents, as described for example in U.S. Pat. No. 6,527,762 (Santini et al.), U.S. Pat. No. 6,491,666 (Santini et al.), U.S. Pat. No. 6,551,838 (Santini et al.), U.S. Pat. No. 7,226,442 (Sheppard et al.), U.S. Patent Application Publication 2004/0121486 (Uhland et al.), U.S. Patent Application Publication 2005/0096587 (Santini et al.), U.S. Patent Application Publication 2005/0267440 (Herman et al.), and U.S. Patent Application Publication 2008/0015494 (Santini et al.), the contents of which are all incorporated herein by reference.

It is generally useful to provide such medical implants 10 with a wireless link to a base station 14 located near the patient 12. As a matter of convenience, it is useful for the wireless link to be such that the patient 12 may stray a limited distance from the base station 14 without interrupting communication. This would enable the wireless link to be used unobtrusively. For example, if the range of the wireless link is on the order of the size of a typical household room, such as a bedroom, or a typical hospital room, and if radiation exits the patient 12 omnidirectionally, it is possible for the patient 12 to be anywhere within the room without disrupting wireless communication between the implant 10 and the base station 14.

As used herein, terms such as "omnidirectional" and "omnidirectionally" are used to describe receiving or sending radio waves equally well in all directions in a principal plane of an antenna. The term "equally well" is not intended to imply strict and unvarying equality but is intended to encompass minor deviations from equality.

Figure 2:
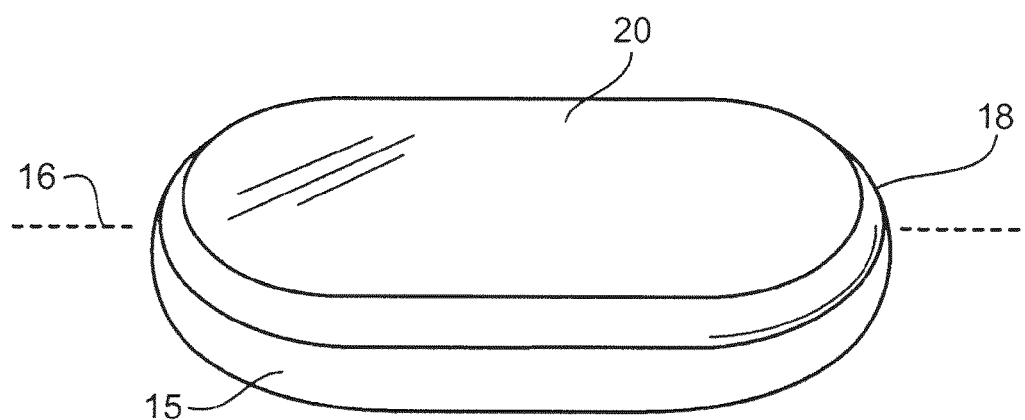
FIG. 2 shows the medical implant of FIG. 1 in more detail.

FIG. 2 shows the medical implant 10 in more detail. The medical implant 10 features a generally elliptical housing 15 having a major axis 16. The housing 15 is typically a biocompatible metal, such as titanium or titanium alloy shell, with the metal forming the shell having a wall thickness of about 0.3 mm. In some embodiments, the overall thickness of the housing 15 is 8.2 mm. In other embodiments, the overall thickness of the housing 15 is 10-11 mm. An elliptical locking ring 18 having similar transverse dimensions as the housing 15 holds an RF transparent cover or dielectric shield 20 in place above an antenna structure (not shown) connected to a transceiver (not shown). The cover 20 functions to protect the antenna structure from contact with bodily fluids and/or tissues. The locking ring 18, like the housing 15, is typically a biocompatible metal, such as titanium. A suitable material for an RF-transparent cover 20 or dielectric shield is non-conducting material, such as polyethylene, having a thickness of about 0.4 mm. Alternately, one could fill the space with a biocompatible epoxy, which would then be the cover 20.

When implanted, orientation of the major axis 16 in a direction parallel to the patient's spine results in an omnidirectional pattern in a plane transverse to the patient's spine. This configuration is thus preferable for signal transmission. However, it may be more comfortable for the patient 12 if the surgeon were to orient the major axis 16 inside the patient 12 in a direction perpendicular to the patient's spine.

In practice, once the device is implanted, it may shift to another orientation. Thus, as a practical matter it may be difficult to precisely control the orientation of the medical implant 10. It is therefore desirable that the overall operation of the communication system be relatively independent of the implant's orientation.

Although the implant 10 may shift its orientation after surgery, one can compensate for any such shift. For example, once the incision has healed, it is possible to determine the orientation of the implant 10. This can be achieved, for example, by X-ray inspection, or by rotating the receiving antenna to identify a radiation maximum. If the implant 10 is sufficiently close to the skin, the orientation can be determined by feeling the implant 10 through the skin. In either case, one can then determine an optimal orientation of the implant 10 relative to the base station 14 for establishing communication with the base station 14. Information representative of this optimal orientation can then be made available for the patient's use in guiding his activities, or for optimally arranging a patient's furnishings, such as the bed and the base station 14, to maximize likelihood of establishing and maintaining such communication while the patient is asleep.

FIG. 3 is a block diagram of the medical implant 10 showing a transceiver 22 having MICS circuitry 24 for communication in the MICS band, and wake-up circuitry 26 for providing a wake up signal to the MICS circuitry 24. Both the MICS circuitry 24 and the wake up circuitry 26 are in communication, through matching circuits 27, 29A, 29B, with a dual band antenna 28 as described in more detail in connection with FIGS. 4 and 5. A controller 30 provides control over both the MICS circuitry 24 and the wake-up circuitry 26. Implant circuitry 32 controls the functions of an implant device 33. A suitable transceiver 22 is the ZL70101 manufactured by Zarlink Semiconductor of Ottawa, Ontario, which is in widespread commercial use in the U.S. and other countries.

The base station 14 and transceiver 22 communicate through two frequency bands: a lower frequency band, such as the MICS band, which extends from 402-405 MHz, and a higher frequency band having frequencies on the order of 2.45 GHz. The MICS band is used primarily for data communication between the transceiver 22 and the base station 14, whereas the higher frequency band is used to provide a wake-up signal to the transceiver 22, but it is not necessary that the transceiver 22 transmit back to the base station 14 at the 2.45 GHz frequency.

FIG. 4 summarizes a procedure used by the base station 14 to establish communication with a medical implant 10. The base station 14 transmits a wake up signal at 2.45 GHz (step 34) and then listens for a response on a MICS frequency (step 36). This wake up signal includes information identifying the particular MICS frequencies to be used. If no response is forthcoming, the base station 14 retransmits the wake up signal (step 34). If the base station 14 detects a response from the implant, it then establishes communication in the MICS band with the implant 10 (step 38).

Meanwhile, the transceiver 22 on the implant 10 carries out a procedure such as that shown in FIG. 5.

According to FIG. 5, the wake-up circuitry 26 of the implant's transceiver 22 periodically listens for a wake up signal at 2.45 GHz (step 40). If no signal is detected (step 42), the controller 30 instructs the wake up circuitry 26 to wait for some pre-selected interval (step 44) and repeats this process (step 40). Otherwise, if the transceiver 22 detects a wake up signal (step 42), it sends a signal to wake up the MICS circuitry 24 (step 46) which then establishes communication with the base station 14 (step 48). In one embodiment, the waiting time is selected to be approximately one minute. In another embodiment, the controller 30 causes the wake-up circuitry 26 to listen for the base station 14 at a particular time. In yet another embodiment, the controller 30 causes the wake-up circuitry 26 to listen for the base station 14 at variable time intervals.

The communication protocol described in FIGS. 4 and 5 is particularly advantageous because the 2.45 GHz signal can be repeatedly broadcast by the base station 14 at relatively high power, and because the wake-up circuitry 26 on the medical implant does not have to consume power by transmitting. Moreover, there is no need to power up the MICS circuitry 24 unless MICS communication is actually required. In addition, since the wake-up signal identifies the portion of the MICS band to be used, there is no need for the MICS circuitry 24 to consume energy scanning across the MICS band to search for a signal.

A difficulty that arises when attempting to communicate with an implanted transceiver 22 is that the tissues that make up the human body generally have complex permittivity. As is well-known in the art, the imaginary term of a complex permittivity results in evanescent waves. Evanescent waves are essentially waves that die away, or decay, with distance from their sources. Such waves cannot be used to carry data over any meaningful distance since they themselves cannot travel any meaningful distance.

Conventional antennas used in medical implants are omnidirectional. However, even though such antennas are omnidirectional, the system formed by the union of the antenna and the human body does not radiate omnidirectionally in the space.

Figure 6:
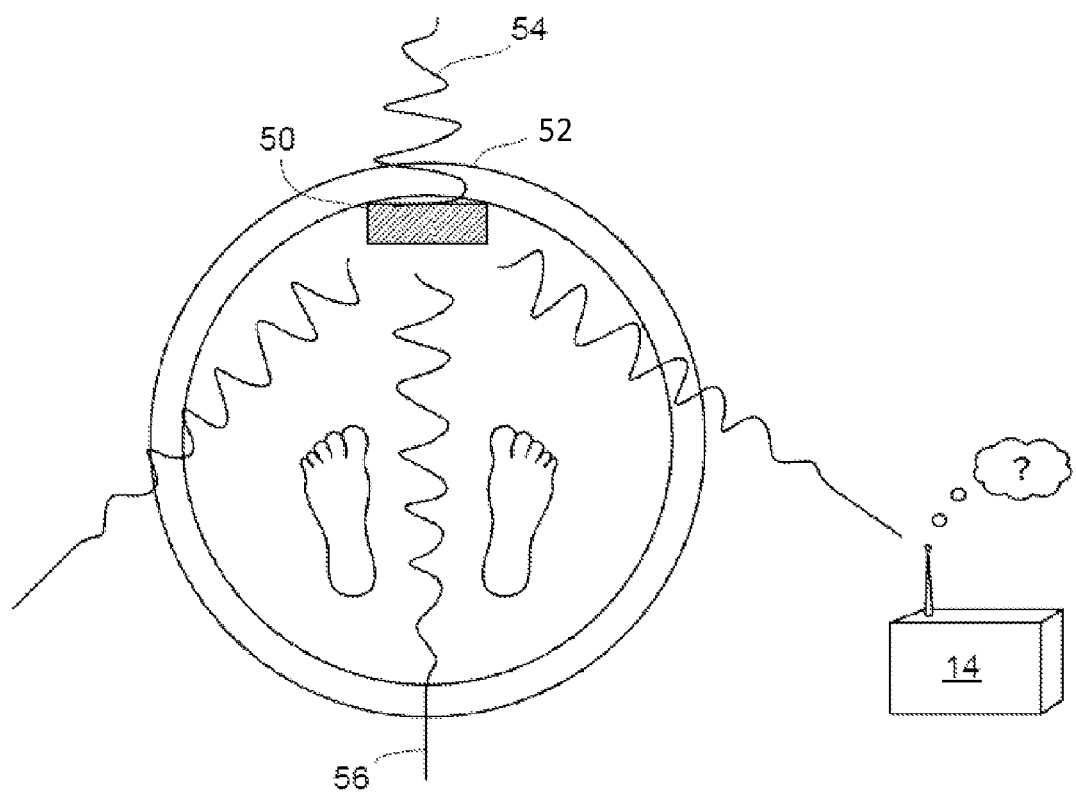
FIG. 6 shows the dissipation of energy associated with a conventional omnidirectional antenna.

FIG. 6 shows a prior art implant 50 located near the ventral surface 52 (i.e., the belly or stomach) of a patient 12. The implant 50 uses a conventional antenna that radiates omnidirectionally in a transverse plane. However, the power that actually leaves the patient's body in a particular direction depends on the path length that the wave must traverse within the body, and the permittivities that the wave encounters before reaching free space. In particular, a wave 54 traveling in a ventral direction experiences little attenuation because the path length before reaching free space is relatively short. In contrast, a wave 56 traveling in the dorsal direction (i.e., toward the spine or back) travels much further within the body, and therefore experiences more significant attenuation.

Figure 7:
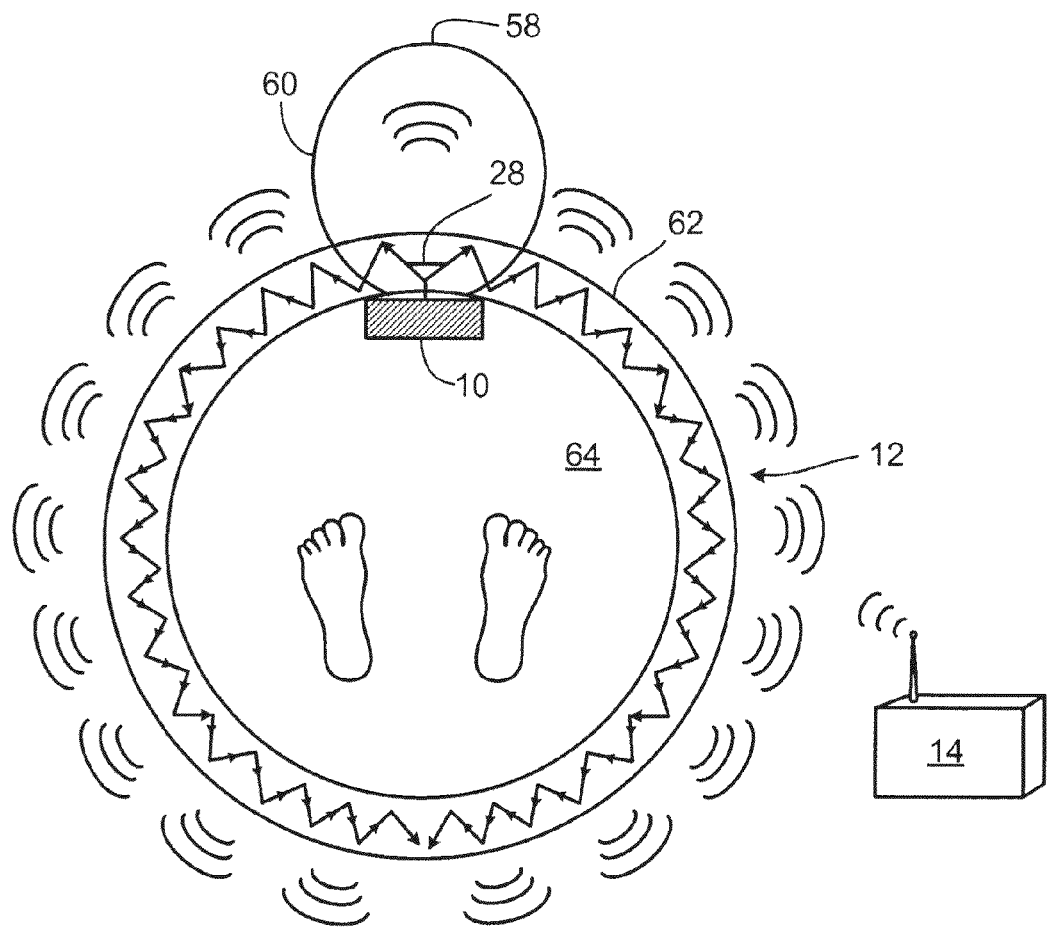
FIG. 7 shows the propagation of endodermal waves associated with the antenna associated with the wireless communication system of FIG. 3.

In contrast to the omnidirectional antenna shown in FIG. 6, an antenna 28 as shown in FIG. 7, and as disclosed herein, provides a beam core 58 directed radially outward, away from the patient's core, and a beam periphery 60 directed to cause energy to enter the patient's peripheral layer 62. As used herein, "peripheral layer" refers to the outermost layers of the body. Accordingly, "peripheral layer" may include the dermal layer and other tissues found in the outermost layers, such as subcutaneous fats, as well as the integumentary layer. The peripheral layer 62 has a permittivity that differs from both the free space permittivity and from the permittivity of the interior 64 of the patient's body. As such, it functions in the manner of a leaky waveguide.

While not wishing to be bound by any particular physical mechanism, the antenna 28 is believed to launch an electromagnetic wave within the peripheral layer 62. Since the wave propagates in the peripheral layer 62, it will be referred to herein as an "endoperipheral wave." As it propagates, the endoperipheral wave encounters two discontinuities in permittivity that define the inner and outer boundaries of the peripheral layer 62. When the endoperipheral wave is incident on the outer boundary, a portion of its energy leaks across the boundary and propagates in free space. The remaining portion is reflected back and continues to propagate endoperipherally.

Figure 22:
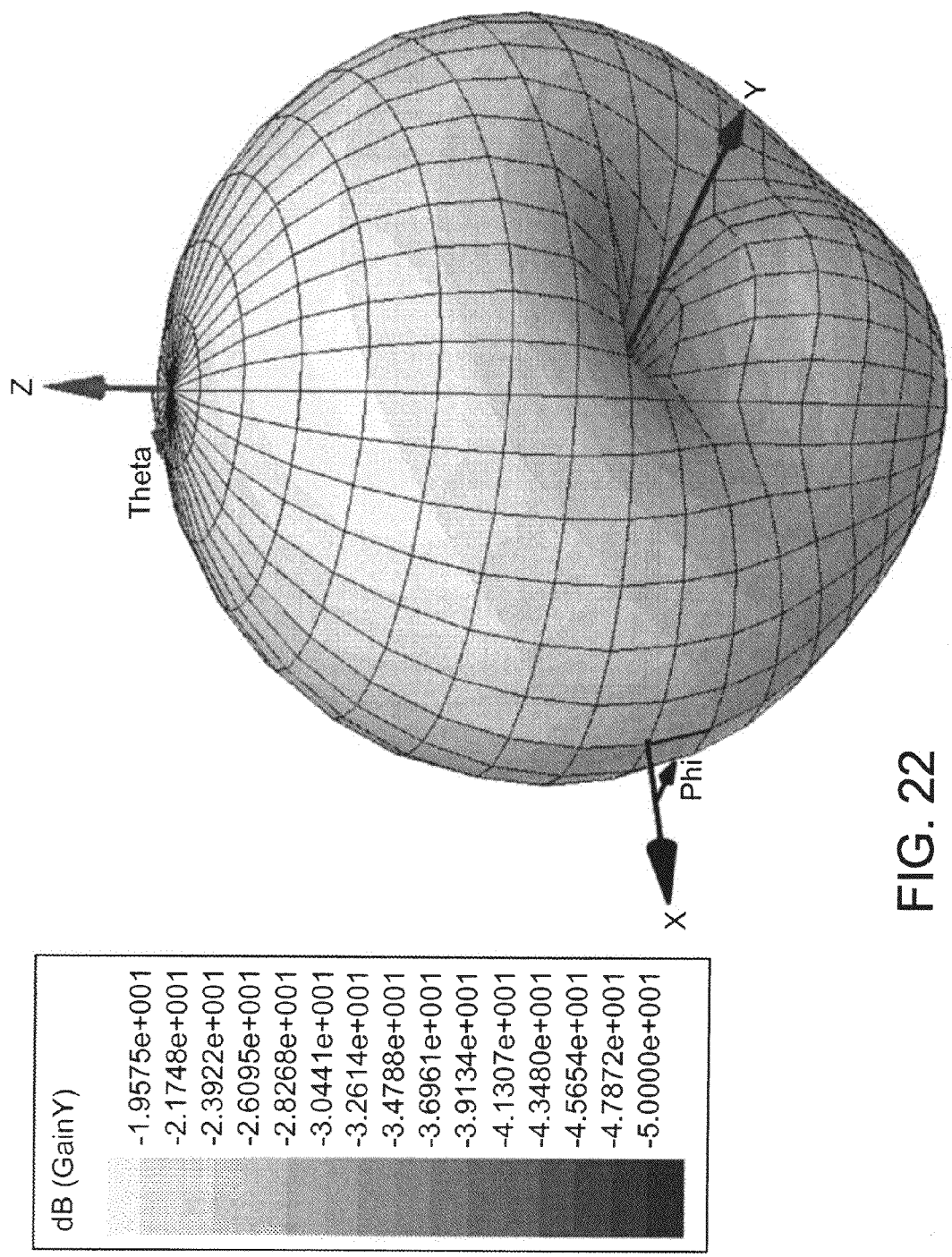
FIGS. 22 and 23 show representative three-dimensional patterns for the antenna system of FIG. 8.
Figure 23:
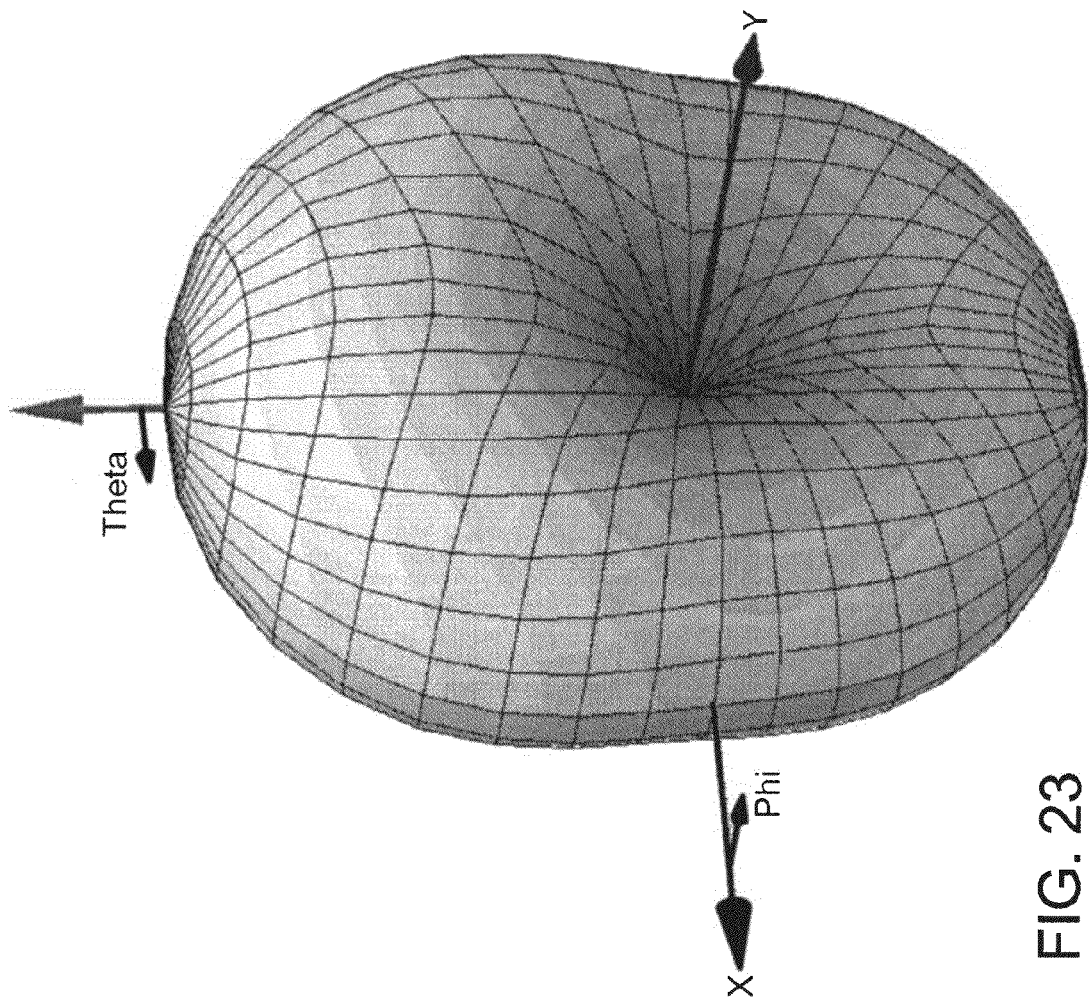

The net effect of the foregoing arrangement as shown in FIG. 7 is a reduction in the dramatically different path lengths shown in FIG. 6. As a result, the combination of the antenna 28 and the human body shown in FIG. 7 radiates in a more omnidirectional manner than the combination shown in FIG. 6, as shown in FIGS. 22 and 23.

The conventional antenna shown in FIG. 6 is an omnidirectional antenna. One might have expected that such an omnidirectional antenna in a medical implant 10 would provide an omnidirectional radiation pattern. But this is not the case.

In contrast, the antenna 28 shown in FIG. 7 is not an omnidirectional antenna; it is a directional antenna. Thus one might have expected that a directional antenna in a medical implant 10 would fail to achieve a nearly omnidirectional pattern.

Contrary to conventional expectation, this is not the case. Instead, the directional antenna 28 interacts in an unexpected way with the patient's anatomy so that even though the antenna 28 itself is directional, the synergy between the directional antenna 28 and the wave propagation properties of the patient's anatomy results in a nearly omnidirectional radiation pattern for the overall system formed by the antenna 28 and the patient 12, as shown in FIGS. 22 and 23.

Figure 8:
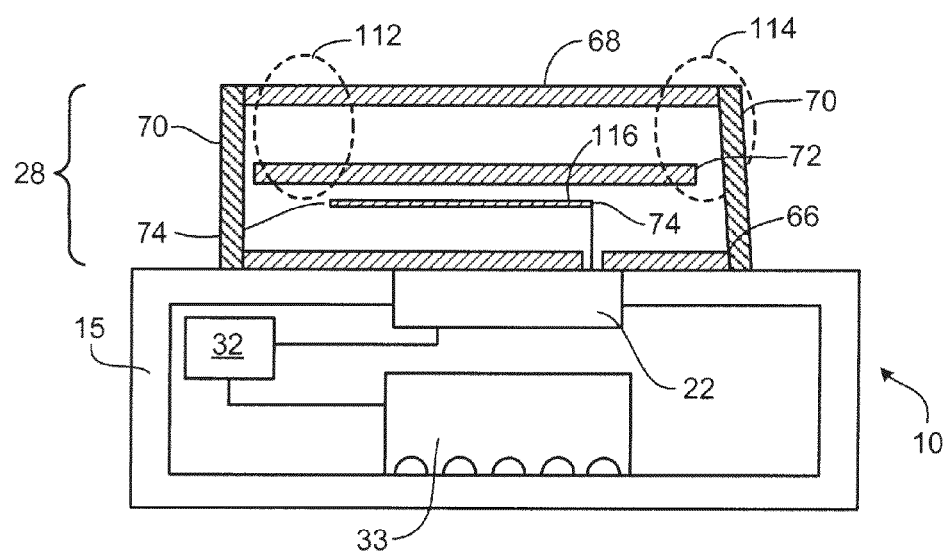
FIG. 8 is a transverse cross section of the medical implant shown in FIG. 2.

FIG. 8 shows a transverse cross section of a medical implant 10 having an antenna 28 for launching electromagnetic waves in the manner described above. The medical implant 10 has a housing 15 on which is disposed a bottom ground plane 66 separated from a top ground plane 68 by a conducting connector 70. The top ground plane 68 and the bottom ground plane 66 may also be referred to as "field stops," "shields," or more generally, as a "metal surfaces," which may or may not be planar, and which may or may not be grounded.

Within the implant housing 15 is the transceiver 22, which transmits information from the body to a base station 14 outside the body or receives information from a base station 14 outside the body. The transceiver 22 communicates with implant circuitry 32 that controls operation of an implant device 33 that interacts with the body. One example of an implant device 33 is a glucose sensor as disclosed by U.S. Patent Pub. 2005/0096587 (Santini), referred to above, which is hereby incorporated by reference. Other examples of implant devices 33 include those that perform physiological measurements and those for releasing various drugs. Between the top ground plane 68 and the bottom ground plane 66 is a radiating archipelago 72 comprising planar, non-wire radiating structures. A feed structure 74 disposed between the bottom ground plane 66 and the radiating archipelago 72 is connected to the transceiver 22 disposed within the housing 15. The feed structure 74, top and bottom ground planes 66, 68, radiating archipelago 72, and the connector 70 and related structures form the antenna 28.

Transceiver 22, implant circuitry 32, and implant device 33 are sealed within the housing 15. Signals are passed into and out of the housing 15 between transceiver 22 and antenna 28 using a feed-through structure 160, which is described in more detail in connection with FIG. 16.

Figure 9:
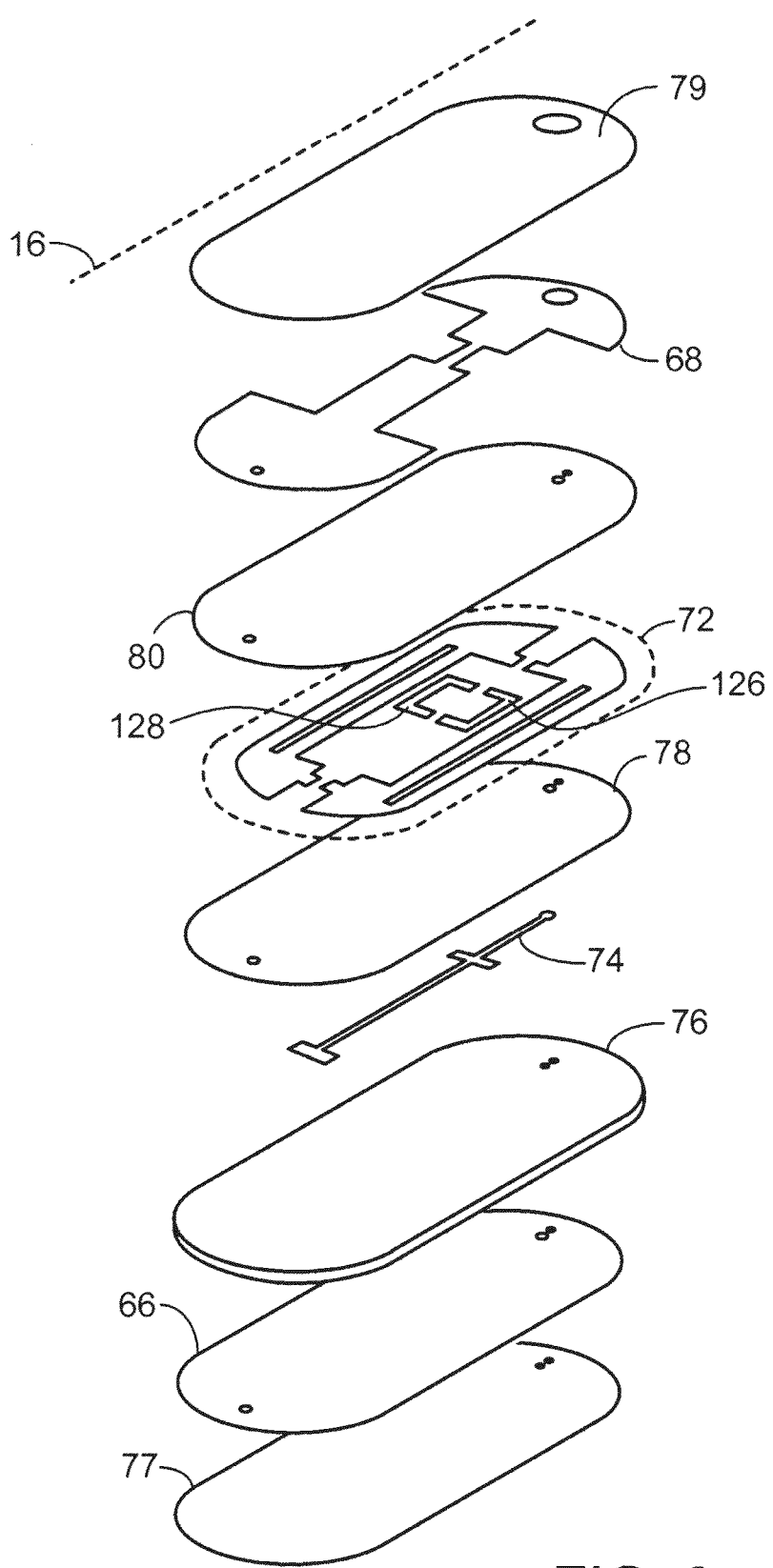
FIG. 9 is an exploded isometric view of the antenna system shown in FIG. 8.

The top and bottom ground planes 68, 66 are separated by a dielectric material, best seen in the exploded view of FIG. 9. As shown in FIG. 9, a first dielectric layer 76 separates the bottom ground plane 66 from the feed structure 74. A second dielectric layer 78 separates the feed structure 74 from the radiating archipelago 72. A third dielectric layer 80 separates the radiating archipelago 72 from the top ground plane 68. A bottom dielectric cover 77 isolates the bottom ground plane 66 from contact with any adjacent conducting media. Similarly, a top dielectric cover 79 isolates the top ground plane 68 from any adjacent conducting media. The top and bottom ground planes 68, 66 are connected by one or more connectors 70, not shown in FIG. 9, that pass through the various dielectric layers. The connectors 70 can typically be vias or metal pins. As a result, the radiating archipelago 72 is capacitively coupled to the feed structure 74 and to the top ground plane 68.

The first dielectric layer 76 is the thickest of the three. The second and third dielectric layers 78, 80 are of approximately equal thickness and significantly thinner than the first dielectric layer 76. The exact thicknesses of each layer depend on the properties of the dielectric and on the wavelengths to be used by the antenna 28. In one embodiment, the first dielectric layer 76 has a thickness of 1.27 mm and the second and third dielectric layers 78, 80 each have a thickness of 0.1 mm.

The thicknesses of the dielectric layers 76, 78, 80 required for optimal radiation characteristics are particularly sensitive to the dielectric's permittivity. In practice, the permittivity of a dielectric varies about some nominal permittivity value from one lot or batch of material from which a dielectric layer is formed to the next lot or batch from which a dielectric layer is formed. Although the variations about the nominal value are small, and may be unimportant in many applications, in the present application such errors are likely to make a significant difference in the performance of the antenna 28.

A suitable dielectric material is a biocompatible material having a high dielectric constant, which tends to reduce the overall dimensions of the antenna. In one embodiment, the dielectric material is alumina having a relative permittivity of 9.5±10% such as that supplied by DuPont under trade designation QM44. However, other dielectrics with relative permittivities between 9 and 10±10% (or higher) are also suitable.

In an effort to promote uniformity in manufacture, it is useful to inspect data provided by the manufacturer concerning the measured permittivity of a particular lot of dielectric. In one practice of manufacturing the antenna 28, one receives, from a supplier of dielectric material used to form dielectric layers 76, 78, 80, a measured value of permittivity associated with a particular lot of dielectric material. This measured actual permittivity is often different from a nominal permittivity. This measured permittivity is then used to determine the thickness of a layer of dielectric required to cause the antenna 28 to have a particular capacitance.

For example, in some manufacturing processes, particularly planar manufacturing processes, the dielectric layers 76, 86, 80 are formed by repeatedly painting and curing individual laminas of dielectric material to build up a layer of dielectric 76, 86, 80 having the desired thickness. In such cases, after having obtained the measured permittivity for a particular lot of dielectric, one can determine the correct number of laminas required to build up a dielectric layer 76, 86, 80 having the desired thickness. One can then provide the manufacturing facility with instructions concerning the correct number of laminas.

Figure 17:
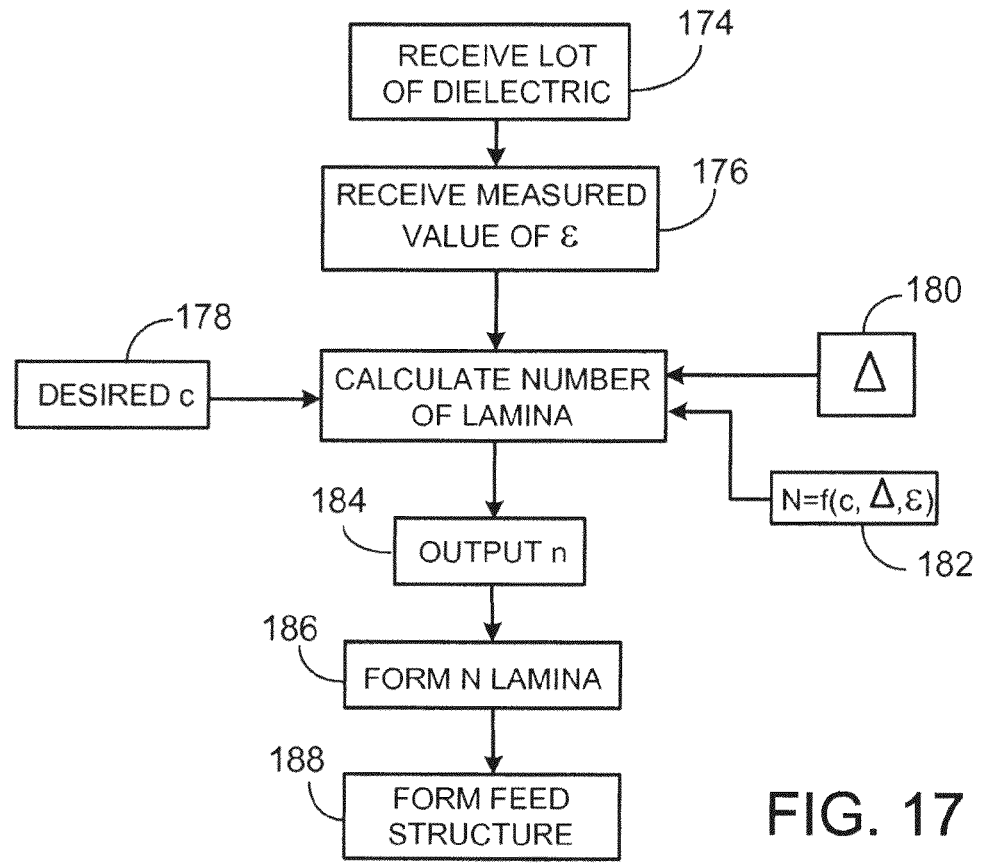
FIG. 17 shows a process for forming a dielectric layer on the antenna system shown in FIG. 8.

Referring to FIG. 17, a process for attaining a desired capacitance includes receiving, from the manufacturer, a lot or batch of particular dielectric (step 174) and a measured value of a permittivity associated with that lot.

The process then includes retrieving the desired capacitance (step 178) and the thickness "d" of a typical lamina of cured dielectric that would be laid down by a particular manufacturing process (step 180). In a typical screen-printing process, this thickness d would correspond to the screen thickness. A value of n, the number of laminas having thickness d required to attain capacitance C is then obtained, either by calculation or by use of a look-up table (step 182). The resulting value, n, of the number of laminas is then output (step 184) and provided to a manufacturing facility. The manufacturing facility then forms the requisite number of laminas to build up a layer of thickness d (step 186) and then forms a feed structure on top of the layer 76 thus formed (step 188). A similar process can be used to build up the second layer 78 and the third layer 80.

In many practices, the thickness of each lamina is constant. However, in some practices of the manufacturing process, the individual laminas have different thicknesses. In such cases, the individual thicknesses are made to sum to the desired thickness.

Figure 10:
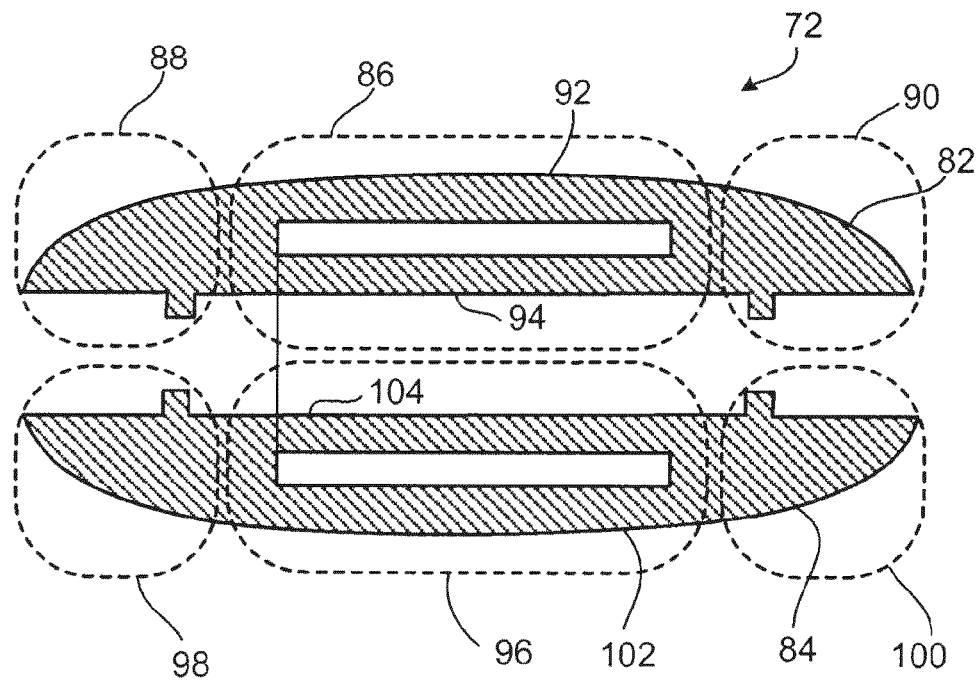
FIG. 10 is a detailed view of the radiating archipelago of the antenna shown in FIG. 8.

FIG. 10 shows the radiating archipelago 72 in detail. The radiating archipelago 72 is made up of twin MICS radiators 82, 84 that are mirror images of each other.

The first MICS radiator 82 includes a radiative portion 86 extending between first and second reactive portions 88, 90 at opposite ends thereof. In the illustrated embodiment, the radiative portion 86 is formed by two generally parallel radiating strips 92, 94 that extend between the first reactive portion 88 at one end of the first MICS radiator 82 and the second reactive portion 90 at the other end of the first MICS radiator 82.

Similarly, the second MICS radiator 84 includes a radiative portion 96 extending between first and second reactive portions 98, 100 at opposite ends thereof. In the illustrated embodiment, the radiative portion 96 is formed by two generally parallel radiating strips 102, 104 that extend between the first reactive portion 98 at one end of the second MICS radiator 84 and the second reactive portion 100 at the other end of the second MICS radiator 84. These radiative strips 102, 104 carry out a function similar to a wire antenna. However, unlike a wire antenna, which is a three-dimensional structure, the radiative strips 92, 94, 102, 104 are essentially two-dimensional structures that can easily be formed using planar processing techniques.

Figure 11:
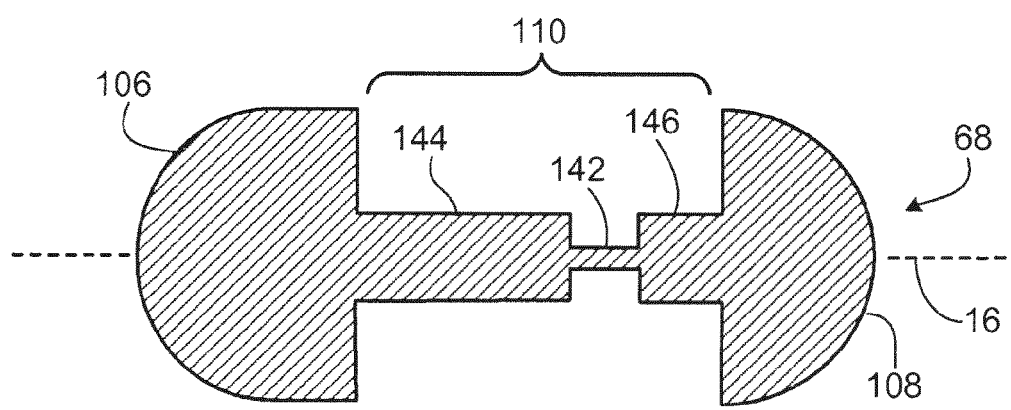
FIG. 11 is a detailed view of the top ground plane of the antenna shown in FIG. 8.

FIG. 11 shows a top ground plane 68 in more detail. The top ground plane 68 includes an enlarged base portion 106 that is connected to the bottom ground plane 66 by one or more connectors 70 through a via. Preferably, vias and connectors 70 are located away from the radiative portions 86, 96 of the first and second MICS radiators 82, 84. At the opposite end of the top ground plane 68 is an enlarged end portion 108 connected to the base portion 106 by an optional neck 110.

The neck 110 is disposed to shield surrounding tissues from stray electric fields generated by the feed structure 74. The base portion 106 is positioned to cover the reactive portions 88, 98 on one end of the twin MICS radiators 82, 84. Similarly, the end portion 108 is positioned to cover the remaining two reactive portions 90, 100 on the opposite end of the twin MICS radiators 82, 84. The particular shapes of the end and base portions 106, 108 are not critical to their overall function.

The end portion 108 of the top ground plane 68 and the two reactive portions 90, 100 of the MICS radiators 82, 84 lie on opposite sides of the third dielectric layer 80. As such, they collectively define a first capacitor 112 between them, as shown in FIG. 8. The base portion 106 of the top ground plane 68 and the two remaining reactive portions 88, 98 also lie on opposite sides of the third dielectric layer 80. As such, they collectively form a second capacitor 114, shown in FIG. 8. Each of these capacitors 112, 114 entraps electric field lines, thus suppressing the tendency of the antenna's near field to heat or to otherwise be dissipated by the human tissue adjacent to the implant 10. Instead of being lost as heat or as dielectric losses, the energy in the near field is available to oscillate from one end of the MICS radiators 82, 84 to the other, preferably at a resonance frequency associated with the MICS radiators 82, 84. As a result, this energy can contribute more significantly to far-field radiation.

Waves that ultimately reach the far field of the antenna 28 originate primarily from the radiative portions 86, 96. Since these radiative portions lie underneath and on opposite sides of the neck 110 of the top ground plane 68, there is little to impede wave propagation from these portions. In embodiments that lack any neck, nothing at all impedes wave propagation. As a result, those waves are free to propagate into the far field of the antenna 28.

As used herein, the "far field" of an antenna, sometimes referred to as the "radiation field," is used in a manner consistent with the way it is used in the antenna arts. In particular, the "far field" is the region of space that is so remote from the antenna that the electromagnetic field of the antenna, which normally includes an evanescent component and a radiating component, consists primarily of the radiating component.

Referring back to FIG. 7, an antenna 28 as described herein provides a pattern having a main lobe 58 that radiates energy in a radial direction away from the patient 12. In addition, some of the energy stored in the near field at the ends of the MICS radiators 82, 84 escapes through the gap between the top and bottom ground planes 66, 68. This energy is manifested as side lobes 60 shown in FIG. 7. It is these side lobes 60 that are believed to provide the energy for launching the endodermal wave.

An antenna 28 as described above has a relatively low radiation efficiency, i.e. only a small portion of energy delivered to the radiative portions 86, 96 is actually radiated. The bulk of the energy remains stored in the near field of the antenna 28 rather than being radiated away.

Figure 14:
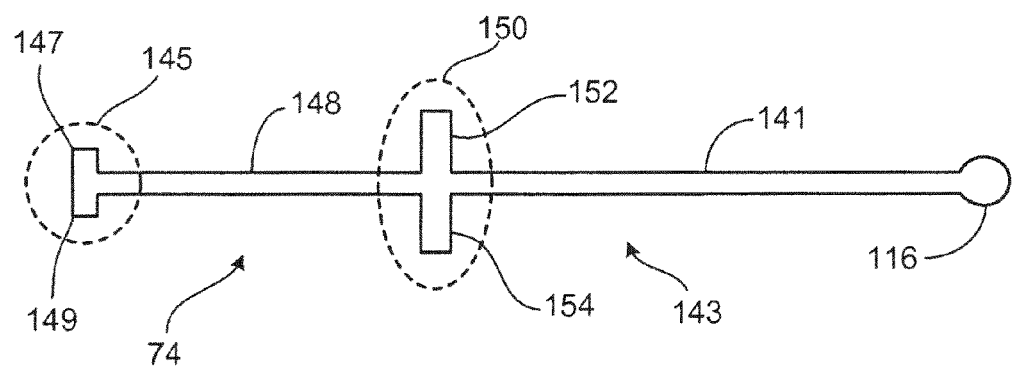
FIG. 14 shows details of the feed structure shown in FIG. 9.

In operation, the transceiver 22 provides energy through a feed point 116, best seen in FIGS. 8 and 14. The energy propagates along the feed structure 74 and couples capacitively to the radiative portions 86, 96. Once on the radiative portions 86, 96, the energy travels towards the reactive portions 90, 100. A small portion of that energy radiates from the relatively inefficient radiating strips 92, 94, 102, 104 of the radiative portions 86, 96. The bulk of the energy reaches the reactive portions 90, 100 and reflects back to travel again along the radiative portions 86, 96, where another small portion radiates away. The remainder then proceeds to the opposite reactive portion 88, 98, which then reflects it back along the radiative portions 86, 96.

The reactive portions 90, 100, 88, 98 and radiative portions 86, 96 thus cooperate to cause energy to oscillate back and forth between the reactive portions 90, 100, 88, 98. At each oscillation, a small portion of that energy radiates away as it traverses the radiative portions 86, 96. Thus, even if the radiation efficiency of each radiative portion 86, 96 is relatively low, the minimal energy radiated with each oscillation accumulates and eventually provides sufficient power to communicate with a base station 14 located at some distance away. For example it is believed that this arrangement will permit communication within the same room approximately five meters away.

The operation of the antenna 28 thus provides another unexpected result. Ordinarily, one would expect to increase range by increasing efficiency, i.e., by providing an antenna 28 that has high radiation resistance. This would translate into a greater fraction of energy being radiated in the far field of the antenna 28. While this may be the desirable solution in free space, the limited space within the human body makes it difficult to implant a large enough antenna to have a high radiation resistance in the MICS band. However, implanting a small antenna with low radiation resistance causes more energy to be retained in the antenna's near field. Since the antenna near field lies within human tissue, this results in dielectric losses.

To overcome the foregoing disadvantage of using an electrically small antenna in a lossy dielectric medium, the reactive portions 90, 100, 88, 98 are shielded by the top ground plane 68. The shielding constrains near fields from spilling out into the surrounding tissue. As a result, dielectric loss is reduced.

Instead of adopting the conventional solution, the antenna 28 described herein is a highly inefficient antenna, i.e., one with a low radiation resistance. In such a highly inefficient antenna, only an insignificant fraction of energy provided to the antenna actually radiates into the far field. Nevertheless, by entrapping the bulk of the energy and bleeding it into the far field a little bit at a time through relatively inefficient radiative portions 86, 96, the antenna 28 avoids losses arising from interaction between its near field and surrounding human tissue. This leads to the unexpected result of an inefficient antenna 28 that nevertheless manages to provide long range wireless communication between a medical implant 10 and a base station as much as 5 meters away.

In operation, the antenna 28 is analogous to a laser oscillator, in which light oscillates between two mirrors with only a small portion of the light escaping through a half-silvered mirror with each oscillation.

The antenna 28 can be viewed as an RLC circuit in which the resonant frequency, which is the reciprocal of the square root of the product of the effective inductance and capacitance, is within the desired frequency band of operation, i.e. the MICS band. The relatively small radiation resistance, as well as the inductance, is provided by the radiative portions 86, 96. The capacitance, which dominates the illustrated configuration, is provided by the two capacitors 112, 114 formed by the interaction between the reactive portions 100, 88, 90, 98 of the MICS radiators 82, 84 and the base and end portions 106, 108 of the top ground plane 68.

Figure 12:
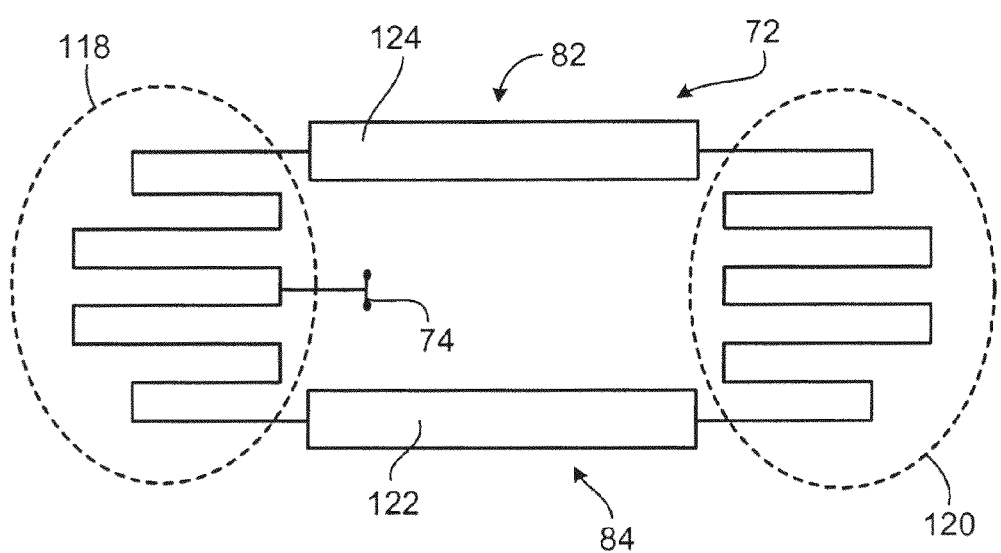
FIG. 12 is an alternative to the radiating archipelago shown in FIG. 10, in which the reactive portions provide an inductance rather than a capacitance.

In another embodiment, the RLC circuit is dominated by inductance rather than capacitance. In that case, the reactive portions of the MICS radiators 82, 84 are meander line structures 118, 120 such as those shown in FIG. 12. In this embodiment, the radiating strips 122, 124 are made somewhat wider so that they can provide the necessary capacitance to tune the antenna 28.

Figure 13:
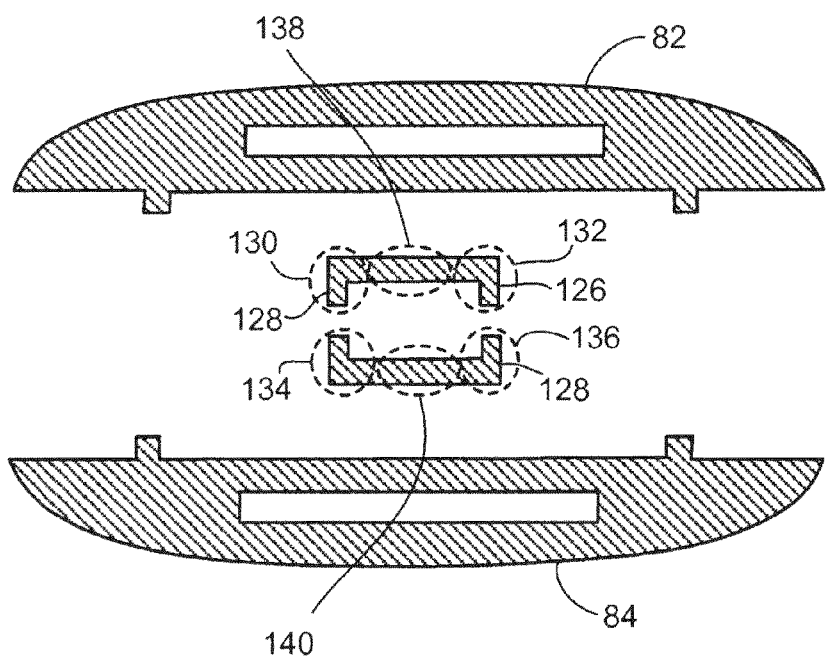
FIG. 13 shows an alternative to the radiating archipelago of FIG. 10.

As discussed above, the transceiver 22, and hence the antenna 28, operates on two frequencies: one in the MICS band and another, in the UHF band, for carrying the wake-up signal. As used herein, "UHF" means one of the ISM (Industrial, Scientific, Medical) bands, and specifically, the ISM band that includes frequencies between 2.4 GHz and 2.5 GHz. To accommodate the second frequency, an alternative embodiment of the radiating archipelago 72 shown in FIG. 13 features UHF radiators 126, 128 tuned to resonate at 2.45 GHz, as shown in FIG. 10. Like the MICS radiators 82, 84, the UHF radiators 126, 128 are twin radiating elements, each one being an essentially linear structure. The first UHF radiator 126 has a first reactive portion 130 and a second reactive portion 132 connected by a radiative portion 138 extending between them. Similarly, the second UHF radiator 128 has a first reactive portion 134 and a second reactive portion 136 connected by a radiative portion 140 extending between them.

As used herein, the use of the term "radiative" portion is not intended to imply that the structure can be used only for transmitting electromagnetic waves. As is well known in the art, antennas are subject to reciprocity. Hence, structures used for transmitting waves have the same properties when used for receiving electromagnetic waves.

Figure 19:
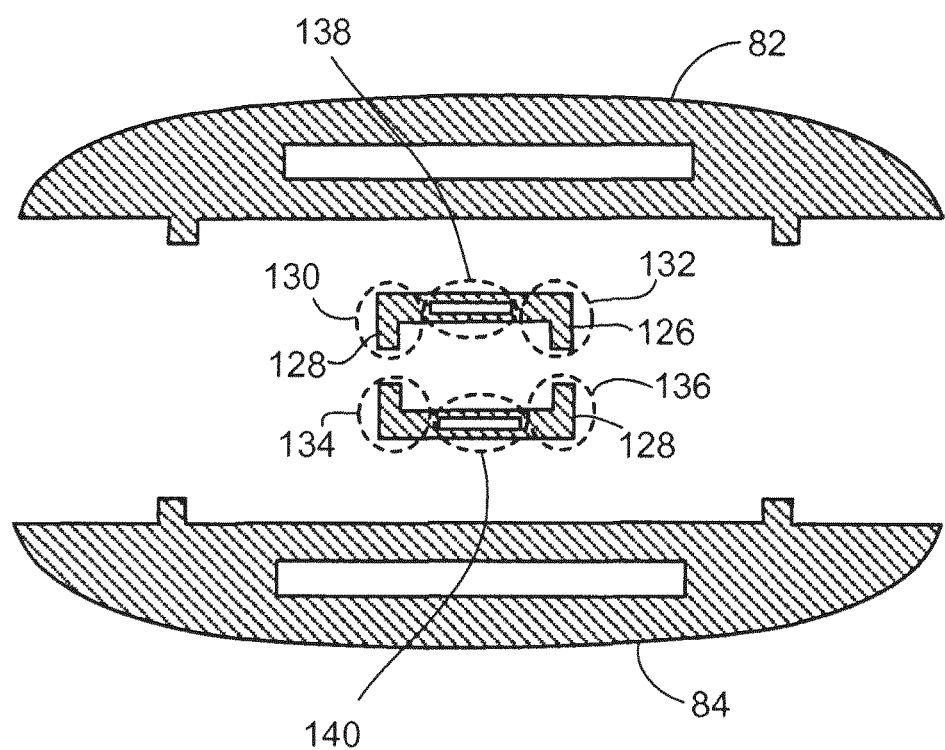
FIG. 19 shows an alternate embodiment of the radiating archipelago of FIG. 13.

In an alternative embodiment, as shown in FIG. 19, the radiative portions 138, 140 of the first and second UHF radiators 126, 128 are formed into radiative strips like those shown on the MICS radiators 82, 84.

As shown in FIG. 11, in those embodiments that include the optional neck 110, the neck 110 can include a central neck 142 and two peripheral necks 144, 146, with each peripheral neck 144, 146 connecting the central neck 142 to one of the end portion 108 and base portion 106. The peripheral necks 144, 146 are both wider than the central neck 142, but not so wide as to interfere with propagation of waves escaping from the radiative portions 82, 84 of the MICS radiators. However, the peripheral neck portions 144, 146 are nevertheless wide enough to form a pair of capacitors with the reactive portions 130, 132, 134, 136 of the twin UHF radiators 126, 128.

It is thus apparent that the operation of the UHF radiators 126, 128 is identical to that of the MICS radiators 82, 84, with the two peripheral neck portions 144, 146 of the top ground plane 68 playing the roles with respect to the UHF radiators 126, 128 that the end and base portions 106, 108 of the top ground plane 68 played with respect to the MICS radiators 82, 84.

In one embodiment, the top ground plane 68 has: (1) a central neck 142 having a length of 4 mm and a width of 1.1 mm; and (2) a pair of 5.1 mm wide peripheral necks 144, 146 having lengths of 6.85 mm long and 10.45 mm respectively. The base portion 106 of the top ground plane 68 is a semicircular region having a radius of 9 mm. The end portion 108 is a semicircular region having a radius of 9 mm contiguous with a rectangular region extending 4 mm towards the base portion 106 and 17.8 mm along a direction perpendicular to the major axis 16 of the implant 10.

A bottom ground plane 66 corresponding to the above top ground plane 68 is a rectangular region extending 25.2 mm along the major axis 16 and 18.82 mm perpendicular to the major axis 16. Each 18.82 mm side of the rectangular region is contiguous with a semicircular region having a radius of approximately 9.4 mm.

Referring now to FIG. 14, the feed structure 74 is an axial transmission line 143 extending from the feed point 116 along the major axis 16. At the distal tip of the axial transmission line 143 is a distal load 145 formed by two short sections 147, 149 of transmission line extending perpendicularly from the axial transmission line 143 in opposite directions underneath the reactive portions 88, 98 of the MICS radiators 82, 84. At an intermediate point of the transmission line, under the UHF radiators 126, 128, is an intermediate load 150 formed by an additional pair of transmission line sections 152, 154 extending perpendicularly from the axial transmission lines 143.

A distal section 148 of the axial transmission line 143 extends between the distal load 145 and the intermediate load 150. A proximal section 141 of the axial transmission line 143 extends between the intermediate load 150 and the feed point 116. A suitable diplexing feed structure 74 for the radiating archipelago 72 whose numerical dimensions have been provided features a distal section 148 having a length of approximately 16.75 mm, and a proximal section 141 having a length of approximately 11.24 mm. The axial transmission line 143, the intermediate load 150 and the distal load 145 cooperate to form a diplexing feed structure 74, or diplexer.

The use of a diplexing feed structure 74 makes it possible to use a single coaxial cable instead of a pair of coaxial cables to provide energy to the feed structure 74. This is particularly advantageous where the device is one in which space is at a premium, for example in a medical implant 10.

However, the use of a diplexing feed structure 74 is by no means mandatory for operation of the antenna 28. The antenna 28 can also be excited by two separate coaxial cables or other transmission lines carrying signals in two different frequency bands.

A suitable diplexing feed structure 74 for the radiating archipelago 72 whose numerical dimensions have been provided features an axial transmission line 143 extending 31.5 mm between the feedpoint 116 and the distal load 145. A pair of 1 mm wide transmission line sections 152, 154 extending 3 mm on either side of the axial transmission line 142 provides the intermediate load 150. A pair of transmission line sections 147, 152 2.5 mm wide extending 1.35 mm on either side of the axial transmission line 143 provides the distal load 144.

Figure 20:
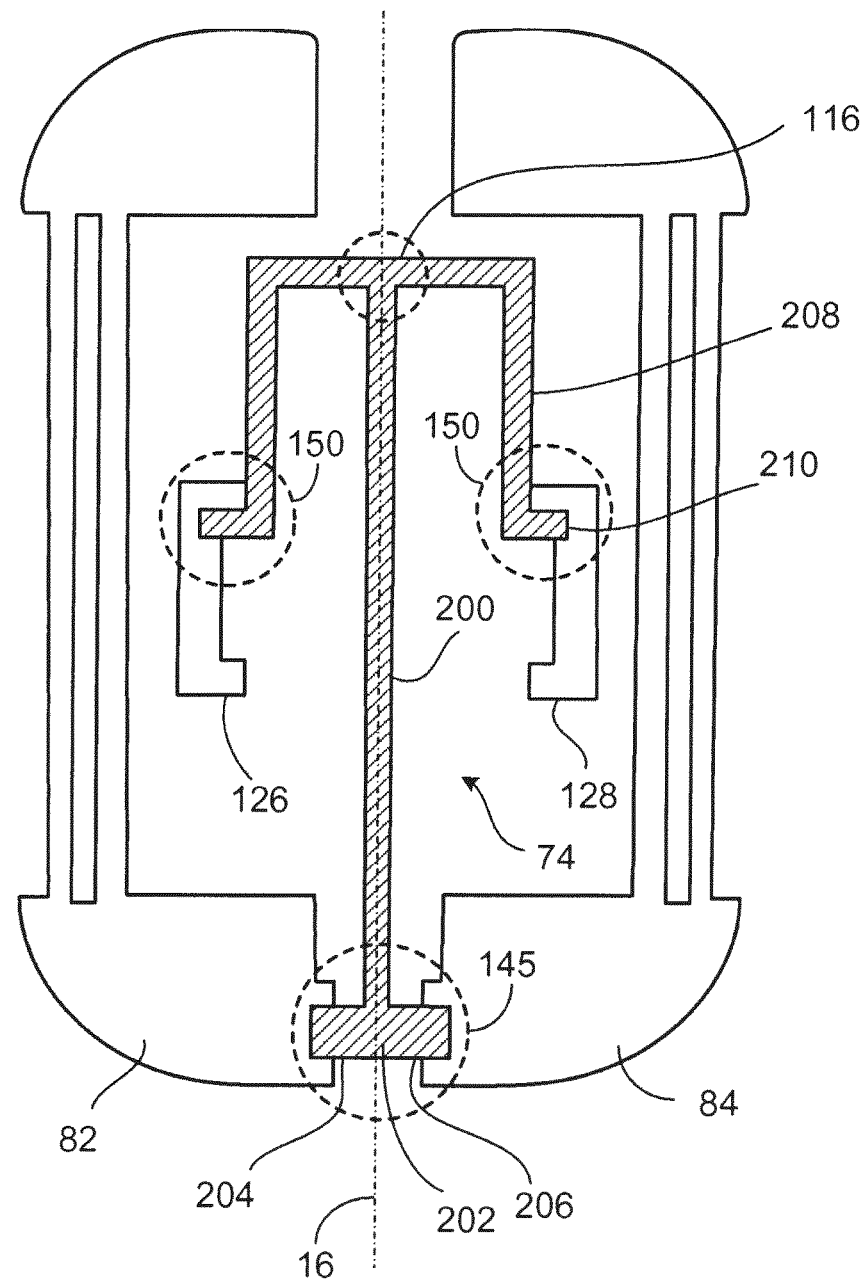
FIGS. 20 and 21 show additional embodiments of a feed structure for the antenna system shown in FIG. 9.

In another embodiment of the feed structure 74, shown in FIG. 20, an axial transmission line 200 extends along the axis 16 of the implant 10 between the feed point 116 and a distal load 202 formed by a pair of transmission line stubs 204, 206 extending perpendicular to the axial transmission line 200 in opposite directions. The distal load 202 is disposed to capacitively couple with the MICS radiators 82, 84. Also extending from the feed point 116 are a pair of transmission lines 208 parallel to and offset from the axial transmission line 200. Each of the pair of transmission lines 208 ends at an intermediate load 210 that capacitively couples to one of the UHF radiators 134, 136.

Figure 21:
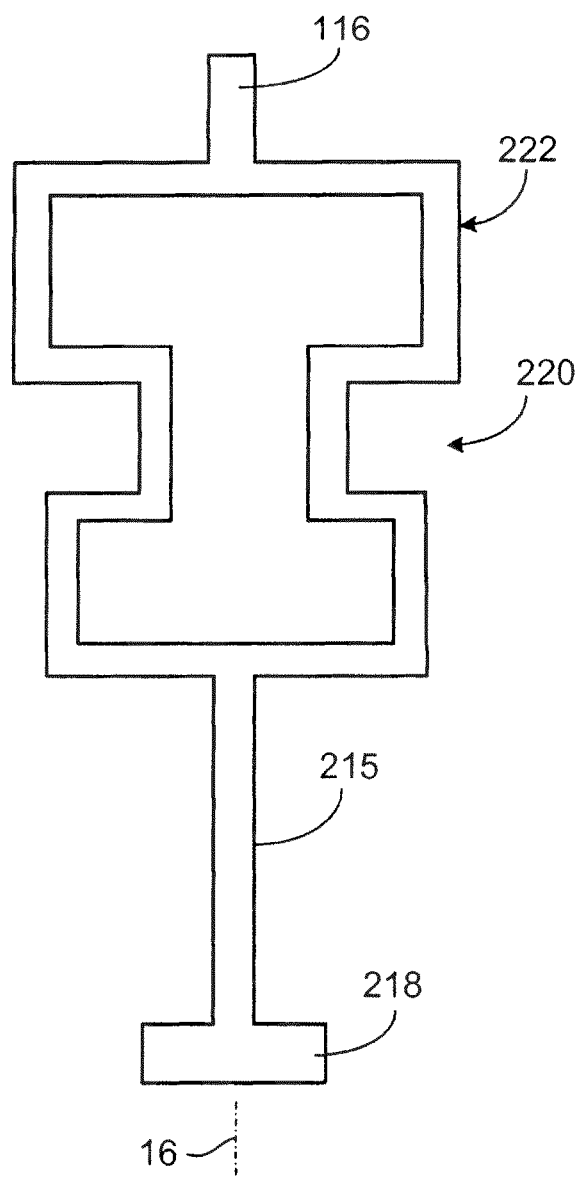

In some embodiments, as shown in FIG. 21, an additional load is provided by introducing a tuning stub formed by proximal and distal right-angle bends in the axial transmission line 143. These two right-angle bends are connected by a connecting section of transmission line parallel to but offset from the axial transmission line 143. The connecting section in one embodiment is 1 mm long and offset by 1.5 mm from the axial transmission line 143. The proximal right-angle bend is approximately 23.7 mm from the feedpoint 116, and the distal right-angle bend is an additional 1 mm further from the feedpoint 116.

In operation, with reference for example to FIG. 14, a wave formed by the superposition of an MICS component and a UHF component originates at the feed point 116 and propagates along the axial transmission line 142. The impedance as seen by the UHF component is such that the distal load 145 appears as an open or short circuit, whereas the intermediate load 150 is matched to the UHF radiators 134, 136. As a result, the UHF component is effectively coupled into the UHF radiators 134, 136 and rejected by the MICS radiators 82, 84. Conversely, the impedance as seen by the MICS component is such that the intermediate load 150 appears as an open or short circuit and the distal load 145 is matched to the MICS radiators 82, 84. As a result, the MICS component is effectively coupled to the MICS radiators 82, 84 and rejected by the UHF radiators 134, 136.

In some embodiments, the impedances are neither those of short circuits nor of open circuits. In these embodiments, the impedances include a finite and non-zero imaginary (i.e., reactive) component. Typically, the reactive component is capacitive; however, for certain configurations the reactive component is inductive.

As shown in the exploded view of FIG. 9, the feed structure 74 is disposed in its own layer between the radiating archipelago 72 and the bottom ground plane 66. A disadvantage of this configuration is that it requires an additional metal layer, and thereby complicates manufacturing. In another embodiment, the feed structure 74 and the radiating archipelago 72 are on the same dielectric layer. In this embodiment, the feed structure 74 is directly connected to selected portions of the radiating archipelago 72 rather than being capacitively coupled to those portions. Such a configuration is less sensitive to errors in manufacture since there is no longer a need to rely on capacitive coupling between the feed structure 74 and the radiating archipelago 72.

Figure 18:
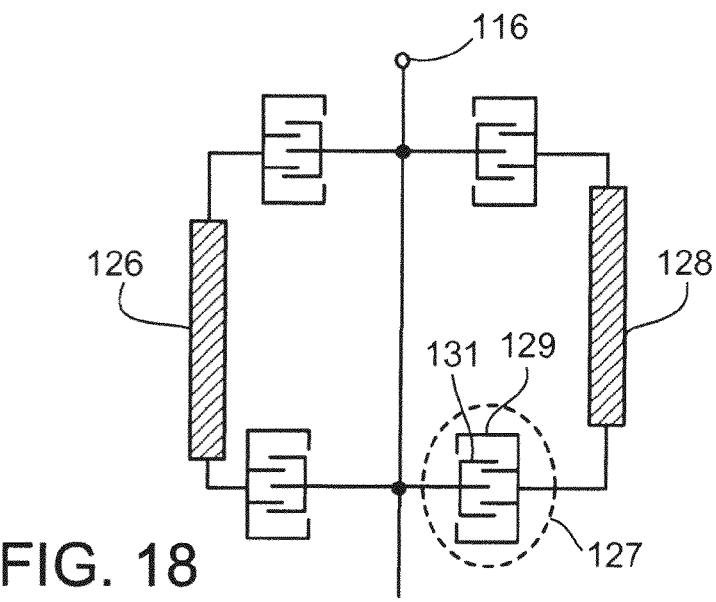
FIG. 18 shows a structure for providing capacitive coupling between an antenna and a feed.

Placement of the feed structure 74 and radiating archipelago 72 on the same layer does not, however, eliminate the possibility of a capacitive coupling between the feed structure 74 and the radiating archipelago 72. For example, FIG. 18 shows UHF radiators 126, 128 capacitively coupled to the feed point 116 using planar capacitors 127 formed by inter-digitating conductive traces 129 connected to the UHF radiators 126, 128 with conductive traces 131 connected to the feed point 116.

In one embodiment, the radiating archipelago 72 extends 15.3 mm from an outermost edge of one outer radiating strip 92 of one MICS radiator 82 to an outermost edge of an outer radiating strip 102 of the other MICS radiator 84, and 36.9 mm from the tip of one reactive portion 88 to the other reactive portion 90. Each radiating strip is about 1.5 mm wide and 21.2 mm long. Each pair of radiating strips 102, 104 is separated by a gap of approximately 0.44 mm. Each UHF radiator 126, 128 has a radiative portion 138 approximately 3.9 mm long and 1 mm wide. Each UHF radiator 126 has reactive portions 130, 134 at each end, with the reactive portions 130, 134 being formed by a metal strip approximately 2.8 mm long and 1 mm wide extending in a direction perpendicular to the radiative portion 138.

Thus, in the MICS band, where the free-space wavelengths are on the order of 0.75 meters, the overall electrical length of the MICS radiators 82, 84 amounts to an insignificant fraction of a wavelength.

Figure 15A:
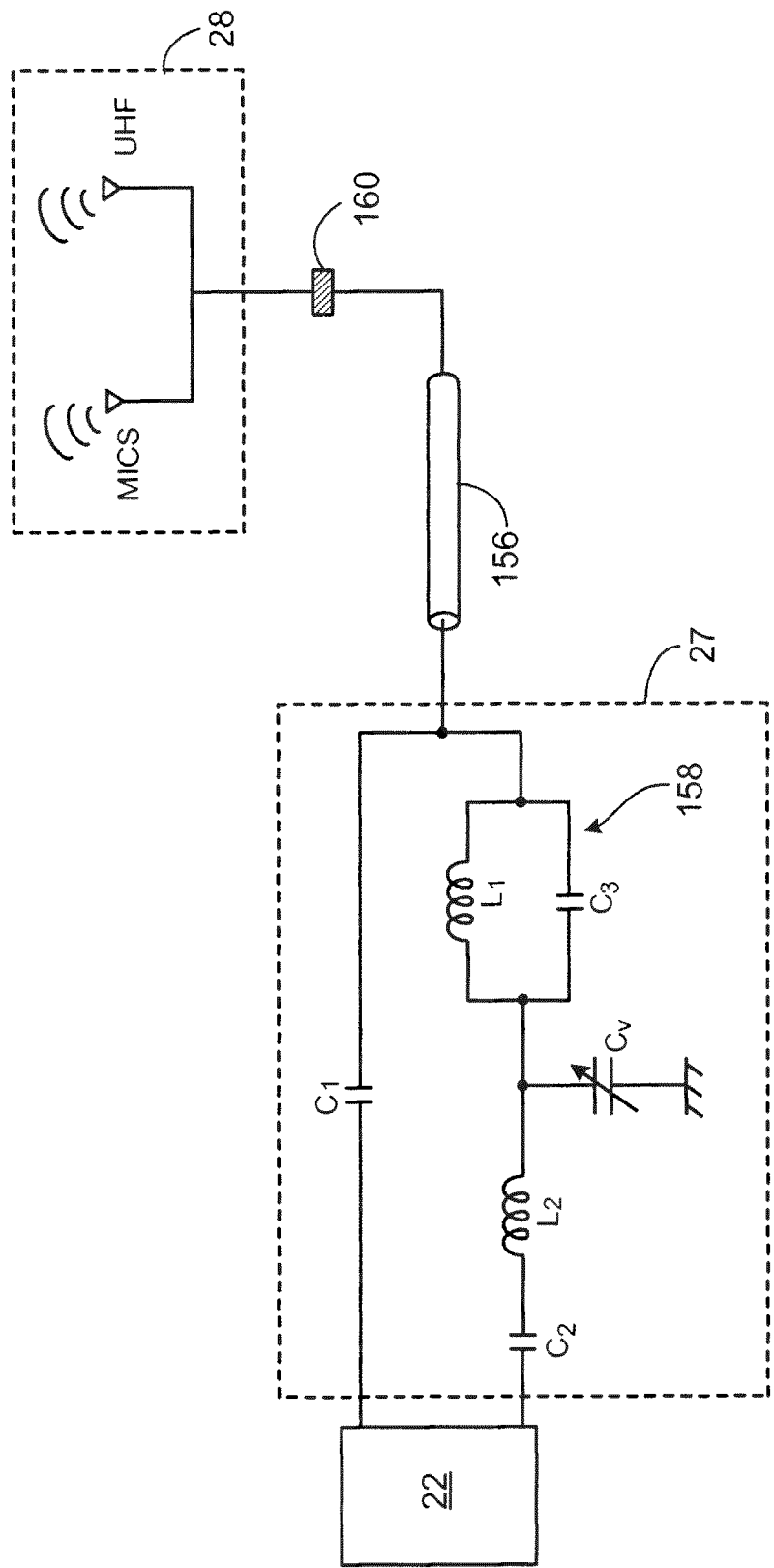
FIGS. 15A and 15B show matching circuits from FIG. 3.

FIG. 15A shows one embodiment of a matching circuit 27 to match the transceiver 22 to the antenna 28. In the illustrated embodiment, the transceiver 22 has an input impedance in the UHF band of 2 kilo-ohms, and an input impedance in the MICS band of 500 ohms when transmitting and 20 kilo-ohms when receiving. The antenna 28 has a 50 ohm input impedance. A coaxial cable 156 with characteristic impedance of 50 ohms connects the antenna 28 to the matching circuit 27.

The illustrated matching circuit 27 features two paths, one for each band. A first path connects the transceiver 22 directly to the antenna 28 by way of coupling capacitor $C_1$. A second path uses a coupling capacitor $C_2$ and coupling inductor $L_2$ to connect the transceiver 22 to the antenna 28 by way of an LC circuit 158 made up of inductor $L_1$ in parallel with capacitor $C_3$. This second path is tuned by a variable shunt capacitor $C_v$.

In one embodiment, coupling capacitor $C_1$ has a capacitance of approximately 0.5 picofarads, coupling capacitor $C_2$ has a capacitance of between about 0.5 and 5 picofarads, coupling inductor $L_2$ has a value between 15 nH and 50 nH, and preferably at or near 22 nH, and the variable capacitance $C_v$ has a capacitance ranging from 5 to 60 picofarads. The LC circuit in this embodiment includes a capacitance $C_3$ of approximately 1 picofarad and an inductance $L_1$ of approximately 3 nanohenries.

Figure 15B:
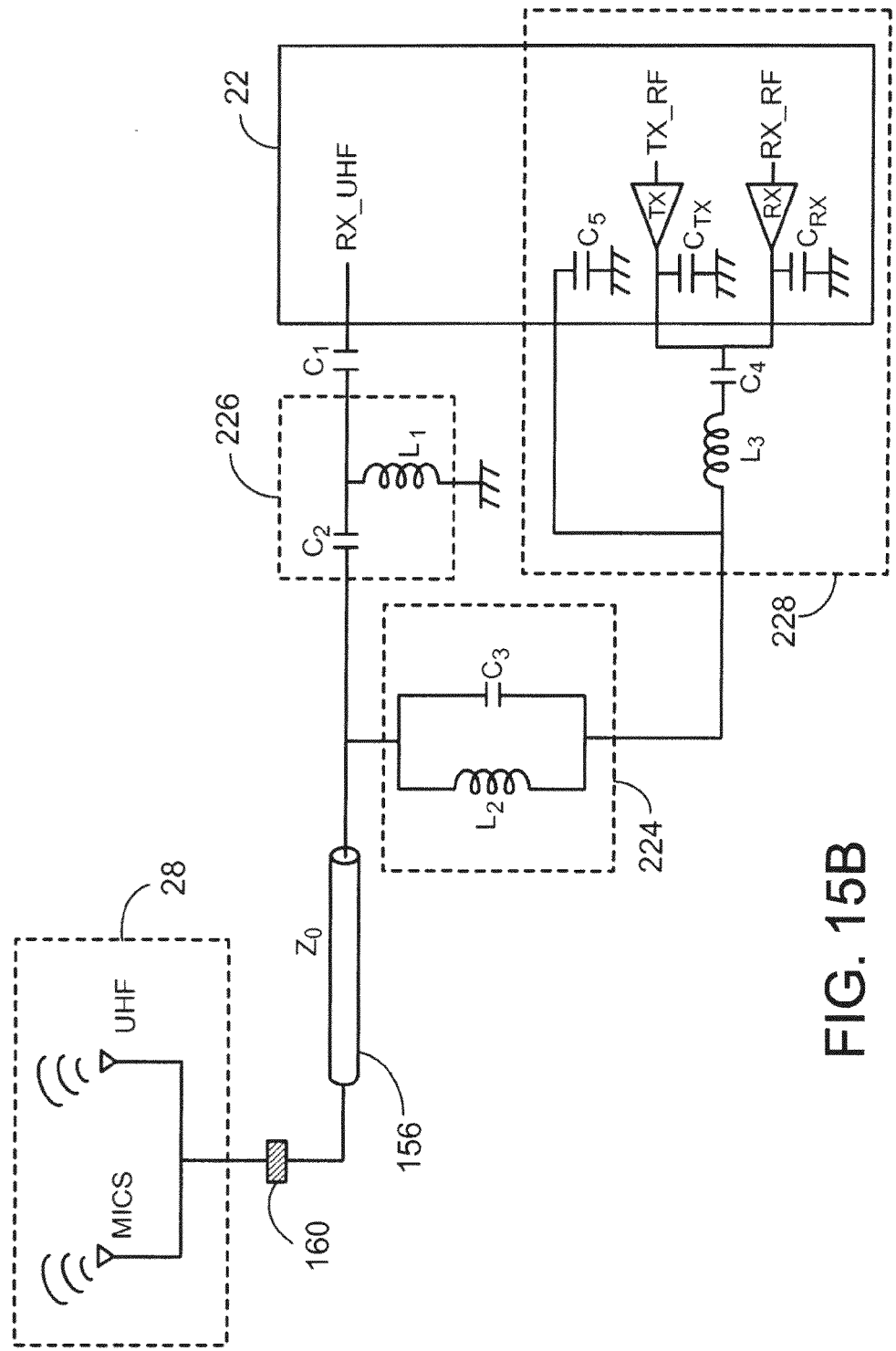

In another embodiment, components within the chip that houses the transceiver 22 are incorporated into the matching circuit 27. Like the matching circuit of FIG. 15A, the matching circuit 27 of FIG. 15B features two paths, one for each band. A first path connects the 2.45 GHz receiving port (RX_UHF) of the transceiver 22 directly to the antenna 28 using a coupling capacitance $C_1$ in series with a high-pass filter 226 formed by a capacitance $C_2$ and inductance $L_1$. A second path uses a stop-band filter 224 formed by capacitor $C_3$ in parallel with inductor $L_2$ in series with a pi-matching network 228. The pi-matching network 228 is formed by an inductor $L_3$ having one terminal connected to ground by a capacitor $C_5$ internal to the chip housing the transceiver 22 and another terminal connected to ground by a DC coupling capacitance $C_4$ in series with parallel capacitors $C_{TX}$ and $C_{RX}$, both of which are also internal to the transceiver 22. The capacitor $C_{TX}$, a transmission port TX-RF of the transceiver 22 by an amplifier TX and the capacitor $C_{RX}$ is coupled to a receiving port RX-RF of the transceiver 22 by an amplifier RX.

Figure 16:
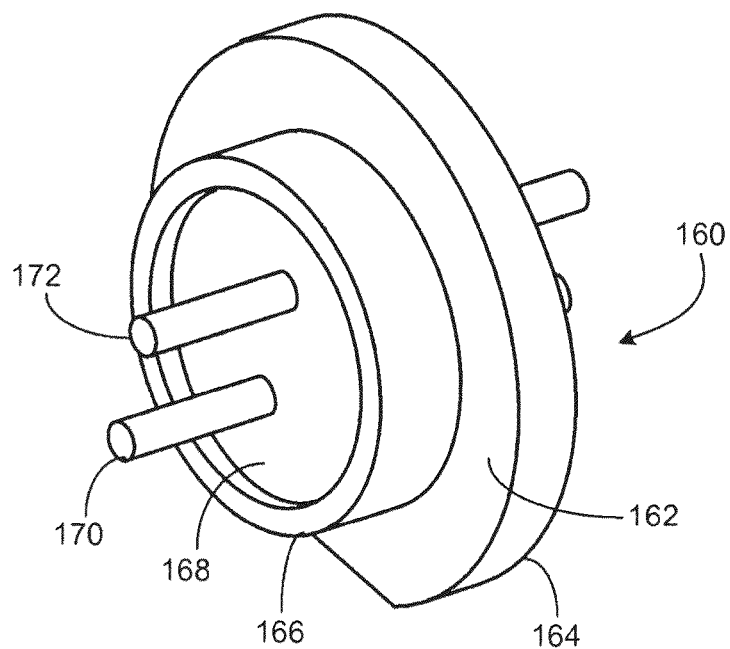
FIG. 16 shows an antenna feed thru for feeding the antenna of FIG. 9.

A feed-through 160, as shown in FIG. 16, provides a connection between the coaxial cable 156 and the antenna 28. This allows the circuit components to be sealed within housing 15 and the antenna 28 to be placed on an external surface of the housing 15. Thus, the RF transparent cover 20 can be made of simple construction to keep the antenna 28 clear of body fluids. The location of the feed-through 160 relative to the matching circuit 27 is shown schematically in FIGS. 15A and 15B.

The feed-through 160 includes an annulus 162 having an outer rim 164 and an inner rim 166. The annulus 162 is sized so that the outer rim 164 engages the sides of a hole in the bottom ground plane 66 at the feed point 116, as shown in FIG. 8. A dielectric plug 168 shown in FIG. 16 fills the space defined by the inner rim 166. First and second conductors 170, 172 extend through the dielectric plug 168. The first conductor 170 extends to the feed structure 74 while the second conductor 172 contacts the bottom ground plane 66. In this way, the feed-through 160 provides electrical contact between the antenna 28 and the matching circuit 27.

FIGS. 22 and 23 show simulated three-dimensional radiation patterns for the antenna at 403.5 MHz (in the MICS band) and at 2.45 GHz respectively. The patterns were computed using the finite-element method as implemented by HFSS software provided by Ansoft Corporation of Pittsburgh, Pa.

In both figures, the y-axis corresponds to the major axis 16 of the housing 15, the z-axis corresponds to the direction away from the patient's body, and the −z direction corresponds to a direction into the patient's body. As is apparent from the figures, at each band there exist nulls in the direction of the major axis and an approximately omnidirectional pattern in a plane transverse to the major axis 16 of the housing 15. As is also apparent from the figures, there exists a small amount of loss in the −z direction that arises as a result of dielectric and conductive losses in the layer amount of tissue that is traversed in that direction.

Figure 24:
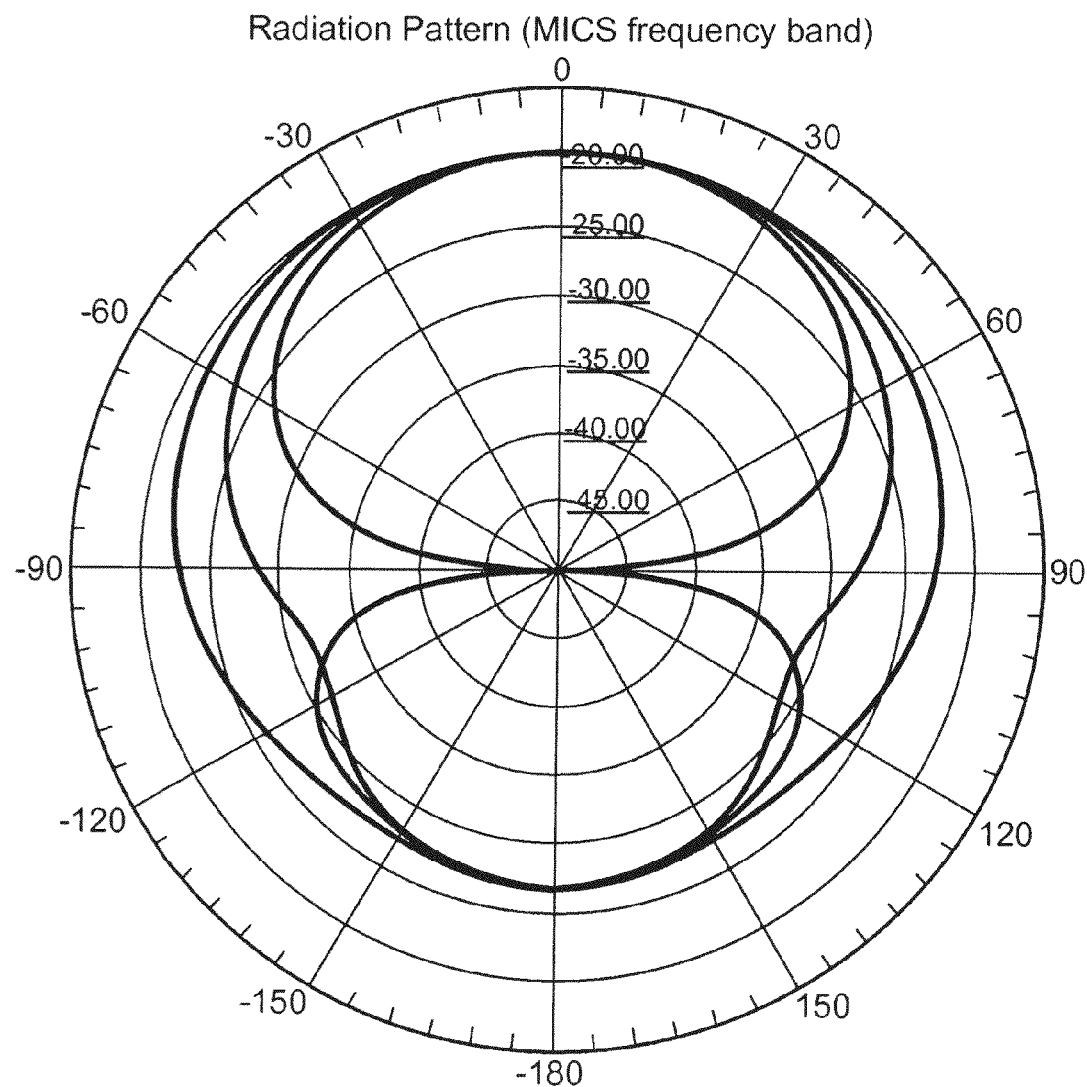
FIGS. 24 and 25 show representative slices through the three-dimensional patterns shown in FIGS. 22 and 23.
Figure 25:
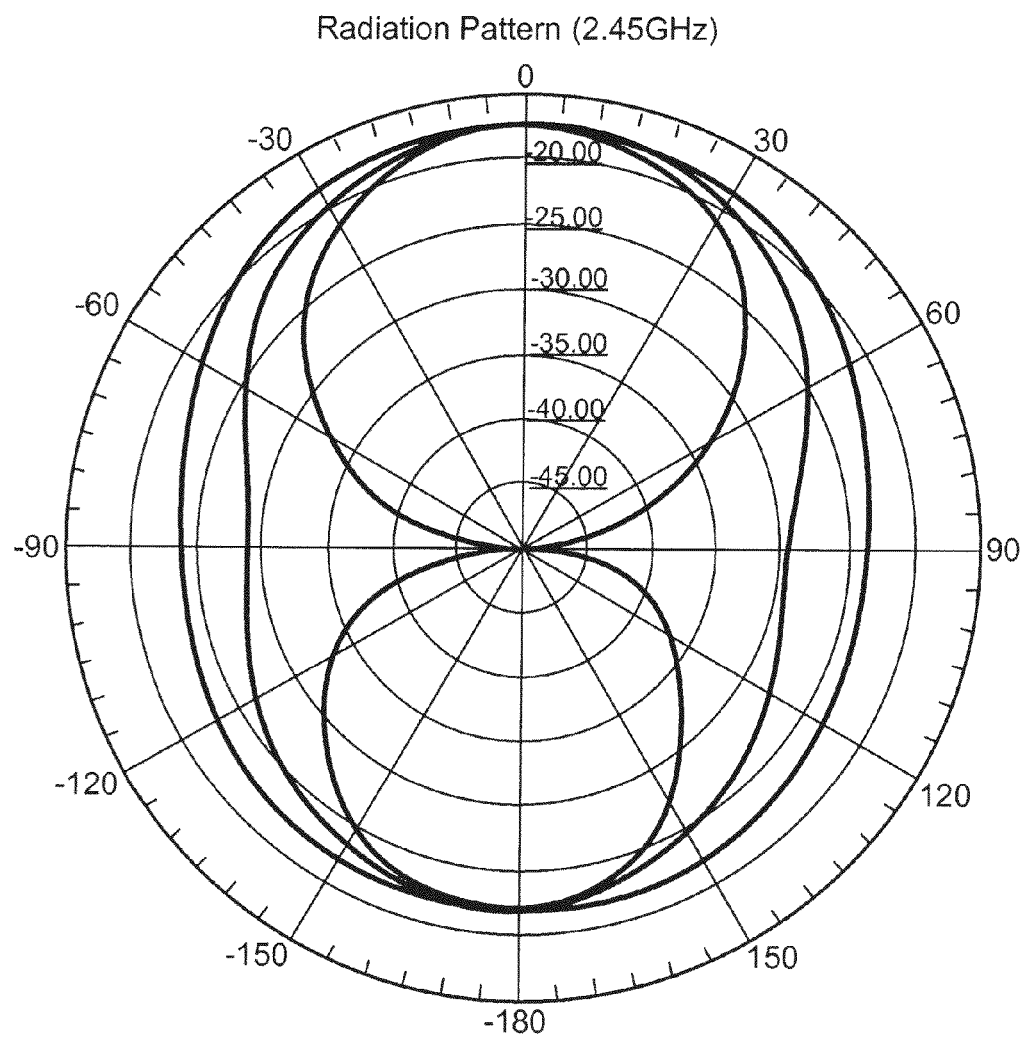

FIGS. 24 and 25 each show three planar slices through the three-dimensional radiation patterns of FIGS. 22 and 23 respectively, one corresponding to a slice containing the yz plane ($\phi=90°$), another containing the xz plane ($\phi=0°$), and a third containing a plane midway between the xz and yz planes ($\phi=45°$).

In an effort to confirm that an antenna as disclosed herein would function as predicted within the MICS band, a link budget was prepared. A constraint imposed on the link budget was that for any direction within 40 degrees of the antenna beam's maximum, the power available at the base station 14 would be at least −90.1 dBm when the transmitted power was −3 dBm. The link budget assumed a −1 dBm loss in the matching circuit and a −2.7 dBm loss for transmission in a direction of forty degrees off-axis.

Transmission across five meters was assumed to result in another −39 dBm loss. A fading margin of −5 dB was assumed in the link budget to account for multipath interference between the antenna and the base station. At the base station 14, the receiving antenna was assumed to have a 0 dB gain and a matching circuit loss of −1 dB.

An antenna as described herein was implanted beneath a layer of fat in pig meat. An antenna gain in the on-axis direction was then measured at frequencies between 360 MHz and 440 MHz in an anechoic chamber using a first antenna under approximately one inch of fat, and using the first antenna and a second antenna under approximately half an inch of fat. The resulting on-axis gains as a function of frequency are shown in FIG. 26.

Figure 26:
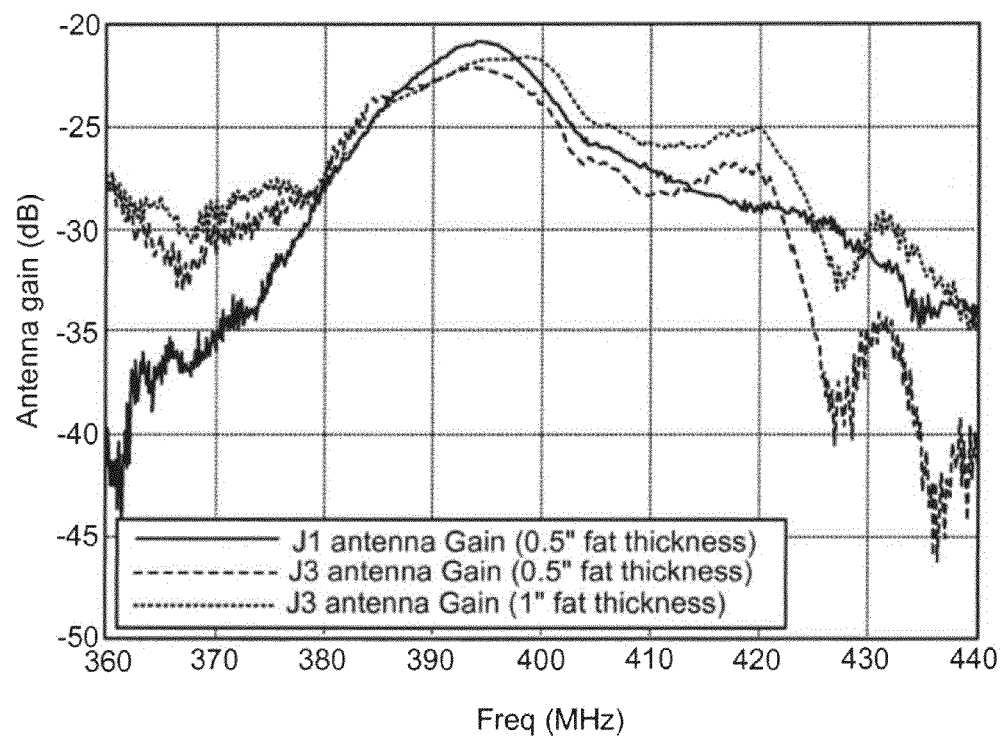
FIGS. 26 and 27 show antenna gain for antennas that have been implanted in a piece of meat.

According to FIG. 26, the on-axis gain at 403.4 MHz was approximately −24 to −25 dB. When this gain was used in the link budget, the power that entered the transceiver 22 following a −3 dBm transmission in a direction 40 degrees off-axis across five meters of free space was found to be adequate for reliable communication.

A similar experiment was carried out for an antenna in the UHF band, specifically at 2.45 GHz. In this experiment, the link budget assumed a transmission of 21 dBm from a base station 14. A matching circuit loss of −1 dB and antenna gain of 0 dB were assumed at the base station 14. Over a five meter free space propagation distance, a loss of −54 dB was assumed, with an additional −2.5 dB loss due to multipath interference. A 0 dB loss was assumed for a matching circuit at the transceiver 22.

Figure 27:
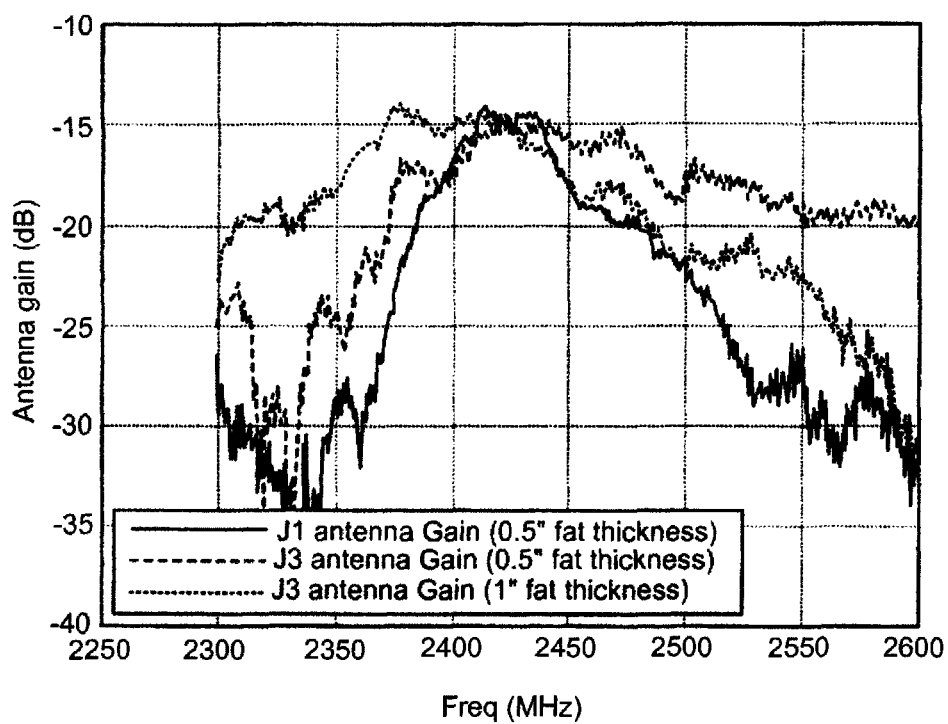

An antenna as described herein was implanted beneath a half inch layer of fat in pig meat. An on-axis antenna gain was then determined in an anechoic chamber by sweeping across a frequency band extending between 2.25 GHz and 2.60 GHz using a first antenna under approximately one inch of fat, and using the first antenna and a second antenna under approximately half an inch of fat. The resulting on-axis gains as a function of frequency are shown in FIG. 27. As is apparent from FIG. 27, the on-axis antenna gain at 2.45 GHz was between approximately −16 dB and −18 dB. When these values of receiving antenna gain were assumed in the link budget, the resulting power available at the transceiver 22 following a 21 dBm transmission from a base station 14 in a direction forty degrees off-axis across five meters of free space was found to be sufficient to reliably detect a wake-up signal at the transceiver 22.

LIST OF REFERENCE NUMERALS

- 10 medical implant
- 12 patient
- 14 base station
- 15 housing of implant
- 16 major axis of implant
- 18 locking ring on housing
- 20 RF-transparent cover
- 22 transceiver
- 24 MICS circuitry
- 26 wake-up circuitry
- 27 matching circuit
- 28 antenna
- 29A, 29B matching circuits (internal to transceiver)
- 30 controller
- 32 implant circuitry
- 33 implant device
- 50 medical implant
- 52 ventral surface of patient
- 54 wave traveling ventrally
- 56 wave traveling dorsally
- 58 main lobe of antenna
- 60 side lobe of antenna
- 62 dermal layer
- 64 interior of patient
- 66 bottom ground plane
- 68 top ground plane
- 70 connector between top and bottom ground planes
- 72 radiating archipelago
- 74 feed structure
- 76, 78, 80 dielectric layers
- 77, 79 dielectric covers
- 82, 84 MICS radiators
- 86, 96 radiative portions of MICS radiators
- 88, 90, 98, 100 reactive portion of MICS radiators
- 92, 94, 102, 104 radiative strips of MICS radiators
- 106 base portion of top ground plane
- 108 end portion of top ground plane
- 110 neck of top ground plane
- 112 first capacitor
- 114 second capacitor
- 116 feed point
- 118, 120 meanderline structures
- 122, 124 radiative strips of meanderline antenna
- 126, 128 UHF radiators
- 127 planar capacitor
- 129, 131 conductive traces of planar capacitor
- 130, 132, 134, 136 reactive portions of UHF radiators
- 138, 140 radiative portions of UHF radiators
- 141 proximal section of axial transmission line
- 142 central neck portion of top shield
- 143 axial transmission line
- 144, 146 peripheral neck portions of top shield
- 145 distal load
- 147, 149 distal load transmission line stubs
- 148 distal section of axial transmission line
- 150 intermediate load
- 152, 154 intermediate load transmission line stubs
- 156 coaxial cable
- 158 LC circuit
- 160 feed through
- 162 frame of feed through
- 164 outer rim of frame
- 166 inner rim of frame
- 168 dielectric plug
- 170 first conductor
- 172 second conductor
- 200 axial transmission line
- 202 distal load
- 204, 206 transmission line stubs
- 208 transmission lines
- 210 intermediate load
- 215 axial transmission line
- 218 distal load
- 220 intermediate load
- 222 transmission
- 224 stop-band filter
- 226 high-pass filter
- 228 pi-matching network Having described the invention and a preferred embodiment thereof, what we claim as new, and secured by Letters Patent is:

What is claimed is:
1. A method for providing transdermal communication, the method comprising:
   causing a current on an antenna implanted inside a patient, the antenna supporting an electromagnetic field having a near-field component and a far-field component;

shielding the near-field component with a grounding structure, thereby trapping energy contained in the near-field component and reducing the extent to which the energy in the near-field component interacts with the patient; and allowing, the propagation of the far-field component through the skin of the patient.

2. The method of claim 1, wherein shielding the near-field component comprises placing a conductive plane between a reactive portion of the antenna and the skin.

3. The method of claim 1, wherein shielding the near-field component comprises placing a conductive plane over a first end of the antenna and a second end of the antenna.

4. The method of claim 1, further comprising selecting the antenna to be a radiating strip.

* * * * *

UNITED STATES PATENT AND TRADEMARK OFFICE
CERTIFICATE OF CORRECTION

| | |
|---|---|
| PATENT NO. | : 8,718,787 B2 |
| APPLICATION NO. | : 13/610394 |
| DATED | : May 6, 2014 |
| INVENTOR(S) | : Utsi et al. |

It is certified that error appears in the above-identified patent and that said Letters Patent is hereby corrected as shown below:

On the title page, item [75] should read:

--Jean-Daniel Richerd, Cambridge, MA--

Signed and Sealed this
Fifteenth Day of July, 2014

Michelle K. Lee
*Deputy Director of the United States Patent and Trademark Office*